(12) United States Patent
Fertig et al.

(10) Patent No.: US 7,423,060 B2
(45) Date of Patent: *Sep. 9, 2008

(54) THIOPHENE HYDROXAMIC ACID DERIVATIVES AND THEIR USE AS HDAC INHIBITORS

(75) Inventors: Georg Fertig, Penzberg (DE); Frank Herting, Sindelsdorf (DE); Matthias Koerner, Antdorf (DE); Manfred Kubbies, Penzberg (DE); Anja Limberg, Penzberg (DE); Ulrike Reiff, Penzberg (DE); Ulrich Tibes, Starnberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 93 days.

This patent is subject to a terminal disclaimer.

(21) Appl. No.: 11/628,772

(22) PCT Filed: Jun. 13, 2005

(86) PCT No.: PCT/EP2005/006294

§ 371 (c)(1),
(2), (4) Date: Dec. 5, 2006

(87) PCT Pub. No.: WO2005/121120

PCT Pub. Date: Dec. 22, 2005

(65) Prior Publication Data

US 2008/0070976 A1 Mar. 20, 2008

(30) Foreign Application Priority Data

Jun. 14, 2004 (EP) .................... 04013860

(51) Int. Cl.
*A61K 31/381* (2006.01)
*C07D 409/14* (2006.01)
(52) U.S. Cl. ........................ 514/444; 549/59
(58) Field of Classification Search ............... 514/444; 549/59
See application file for complete search history.

(56) References Cited

U.S. PATENT DOCUMENTS

| 6,541,661 | B1 | 4/2003 | Delorme et al. |
| 2004/0122079 | A1 | 6/2004 | Grossmann et al. |
| 2004/0214862 | A1 | 10/2004 | Leser-Reiff et al. |

FOREIGN PATENT DOCUMENTS

| WO | WO 01/38322 | 5/2001 |
| WO | WO 03/011851 | 2/2003 |
| WO | WO 03/076395 | 9/2003 |
| WO | WO 03/076430 | 9/2003 |
| WO | WO 03/076438 | 9/2003 |
| WO | WO 03/087066 | 10/2003 |

OTHER PUBLICATIONS

Ranadive, V. B. et al., Indian Journal of Chemistry Section B: Organic Incl. Medicinal Publications & Informations Directorate, New Delhi, In. vol. 12, No. 33 B, Dec. 1994 pp. 1175-1177.
Khan, Mohammed, J. Chem. Soc. Perkin Trans. vol. 2 (1988) (2) pp. 213-219.
Kobashi, Kyoichi et al., Biochem. Biophys. Acta (1971) vol. 227 (2) pp. 429-441.
Sternson, S. M. et al., Organic Letters, vol. 3 (26), (Dec. 2001) pp. 4239-4242 XP002220922.

*Primary Examiner*—Taofiq A Solola
(74) *Attorney, Agent, or Firm*—George W. Johnston; Patricia S. Rocha-Tramaloni; Gene J. Yao

(57) ABSTRACT

Objects of the present invention are the compounds of formula (I) their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

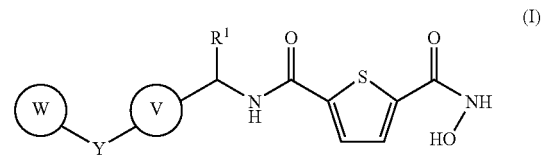

12 Claims, No Drawings

THIOPHENE HYDROXAMIC ACID DERIVATIVES AND THEIR USE AS HDAC INHIBITORS

This application is the National Stage of International Application No. PCT/EP2005/006294, filed Jun. 13, 2005, which claims the benefit of European Application No. 04013860.4, filed Jun. 14, 2004, which is hereby incorporated by reference in its entirety.

The present invention relates to novel thiophene dicarboxylic acid derivatives and to their (R)- and (S)-enantiomers and racemates, to a process for their manufacture, medicaments containing them and their manufacture as well as the use of these compounds as pharmaceutically active agents.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Several structural classes of HDAC inhibitors have been identified and are reviewed in Marks, P. A., et al., J. Nat. Cancer Inst. 92 (2000) 1210-1216. More specifically, WO 98/55449, U.S. Pat. No. 5,369,108, WO 01/38322, WO 01/70675, WO 02/22577, WO 03/011851, WO 03/066579, WO 03/075929, WO 03/076395, WO 03/076400, WO 03/076401, WO 03/076421, WO 03/076422, WO 03/076430, WO 03/076438, WO 03/087066 and WO 2004/013130 report alkanoyl, alkylenyl, alkenylenyl, aryl, heteroaryl, benzyl, biaryl and cinnamyl hydroxamates with HDAC inhibitory activity.

However there remains a need for new compounds with improved therapeutic properties, such as enhanced activity, decreased toxicity, better solubility and improved pharmacokinetic profile, to name only a few.

The present invention relates to thiophene dicarboxylic acid derivatives and to their (R)- and (S)-enantiomers and racemates according to formula I formula I

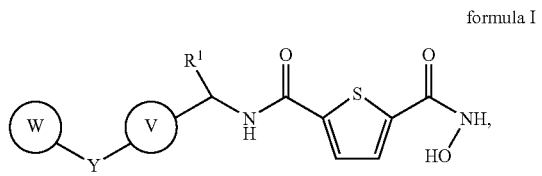

wherein $R^1$ is alkyl, which is optionally substituted one or several times by halogen;

V is phenylene or heteroarylene;

Y —O—;
—O—CHR$^2$—;
-alkylene-O—;
-alkylene-O—CHR$^2$—;
—NH—;
—NH—CHR$^2$—;
-allylene-NH—;
-alkylene-NH—CHR$^2$—; or
-alkenylene-;

$R^2$ alkyl or hydrogen;

W is a saturated carbocyclic group;
a saturated heterocyclic group;
a heteroaryl group; or
a substituted phenyl group, and all pharmaceutically acceptable salts thereof.

The compounds according to this invention are inhibitors of histone deacetylase (HDAC) and therefore possess antiproliferative activity. Objects of the present invention are the compounds of formula I and their pharmaceutically acceptable salts, diastereoisomers, racemates and especially their enantiomeric forms, the preparation of the compounds, medicaments containing such compounds and the manufacture of such medicaments as well as the use of such compounds in the control or prevention of illnesses, especially of illnesses and disorders as mentioned below or in the manufacture of corresponding medicaments.

Examples of tumors which may be treated with such compounds or medicaments, are colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

As used herein, the term "alkyl" means a saturated, straight-chain or branched-chain hydrocarbon containing from 1 to 6, preferably from 1 to 3, carbon atoms, such as methyl, ethyl, n-propyl, isopropyl, n-butyl, 2-butyl, t-butyl.

If said alkyl group is optionally substituted with one or several halogen atoms, it is preferably substituted with chlorine and fluorine, especially fluorine. Examples are difluoromethyl, trifluoromethyl, 2,2,2-trifluoroethyl, perfluoroethyl and the like.

The term "halogen" as used herein denotes fluorine, chlorine and bromine, preferably fluorine and chlorine.

The term "heteroarylene" means a mono- or bicyclic aromatic ring with 5 to 10 ring atoms, which contains up to 3, preferably 1 or 2 heteroatoms selected independently from N, O or S and the remaining ring atoms being carbon atoms. Such heteroarylenes may be optionally substituted one or two times by alkyl which is defined as above, preferably by methyl. Examples of such heteroarylenes are thiophenediyl, isoxazolediyl, pyrrolidinyl, methylthiophenediyl, furandiyl, imidazoldiyl, pyridinediyl, pyrimidinediyl, pyrazinediyl, pyridazinediyl, triazinediyl, pyrazolediyl, oxazolediyl, methylisoxazolediyl, thiazolediyl, isothiazolediyl, thiadiazolediyl, oxadiazolediyl, triazolediyl, benzothiophenediyl, indolediyl, quinolinediyl, isoquinolinediyl, benzofurandiyl and the like, preferably thiophenediyl, isoxazolediyl, pyrrolediyl, especially thiophenediyl, or especially isoxazolediyl.

As used herein, the term "alkylene" means a saturated, straight-chain or branched-chain, preferably straight-chain hydrocarbon containing from 1 to 5, preferably from 1 to 3, carbon atoms, such as methylene, ethylene, trimethylene; tetramethylene, pentamethylene, methylmethylene, methylethylene (propylene), ethylethylene, propylethylene, 1-methyltrimethylene, 2-methyltrimethylene, 1-ethyl trimethylene, 2-ethyltrimethylene.

As used herein, the term "alkenylene" means a unsaturated, straight-chain or branched-chain, preferably straight-chain hydrocarbon containing from 2 to 6, preferably from 2 to 4, carbon atoms. Examples of such "alkenylenes" are vinylene (ethenylene), allylene, isopropenylene, 1-propenylene, 2-methyl-1-propenylene, 1-butenylene, 2-butenylene, 3-butenylene, 2-ethyl-1-butenylene, 3-methyl-2-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene and 5-hexenylene.

The term "saturated carbocyclic group" means a monocyclic saturated hydrocarbon ring with 3 to 7 ring atoms. Such saturated carbocyclic groups may be optionally substituted one or two times by alkyl which is defined as above, preferably by methyl. Examples of such saturated carbocyclic groups are cyclopropyl, cyclobutyl, and cycloheptyl, preferably cyclopentyl or cyclohexyl.

The term "saturated heterocyclic group" means a saturated, monocyclic hydrocarbon ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by alkyl, which is defined as above, preferably by methyl. Examples of such saturated heterocyclic groups are pyrrolidinyl, morpholino, piperazinyl, N-methyl-piperazinyl or piperidyl.

The term "heteroaryl group" means a mono- or bicyclic aromatic ring with 5 to 10 ring atoms, which contains up to 3, preferably 1 or 2 heteroatoms selected independently from N, O or S and the remaining ring atoms being carbon atoms. Such heteroaryl groups may be optionally substituted one or two times by halogen, —CN, —C(O)OH, —C(O)CH$_3$, —SCH$_3$, —NH$_2$, —CH$_2$NH$_2$, —CH$_2$OH or alkyl, preferably by alkyl, wherein alkyl and halogen are defined as above. Examples of such heteroaryl groups are thiophenyl, methylthiophenyl, pyrazolyl, dimethylisoxazolyl, pyridyl, benzothiophenyl, indolyl, furyl, pyrrolyl, imidazolyl, pyrimidyl, pyrazinyl, pyridazinyl, triazinyl, oxazolyl, isoxazolyl, thiazolyl, isothiazolyl, thiadiazolyl, oxadiazolyl, triazolyl, quinolyl, isoquinolyl, benzofuranyl and the like, preferably thiophenyl, methylthiophenyl, pyrazolyl, dimethylisoxazolyl, pyridyl, benzothiophenyl or indolyl.

The term "substituted phenyl group" means a phenyl which is substituted one to three times by alkyl, halogen, —O-alkyl, —S(O)$_2$-alkyl, —NH(alkyl) or —N(alkyl)$_2$; wherein alkyl and halogen are defined as above and the alkyl groups may be optionally substituted with one or several halogen atoms, preferably with chlorine and fluorine, especially fluorine.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

An embodiment of the invention are the compounds of formula I, wherein
W is a saturated carbocyclic group.

An embodiment of the invention are the compounds of formula I, wherein
W is a saturated heterocyclic group.

An embodiment of the invention are the compounds of formula I, wherein
W is a heteroaryl group.

An embodiment of the invention are the compounds of formula I, wherein
W is a substituted phenyl group.

An embodiment of the invention are the compounds of formula I, wherein
$R^1$ is (C$_1$-C$_3$)alkyl;
V is phenylene;
Y -alkylene-O— or
   -alkylene-NH—;
W is a phenyl group,
   which is substituted one to three, preferably one or two, times by alkyl, halogen, —O-alkyl, —S(O)$_2$-alkyl, —NH(alkyl) or —N(alkyl)$_2$; preferably by alkyl,
   and wherein the alkyl group may be optionally substituted with one or several halogen atoms, preferably with chlorine and fluorine, especially with fluorine.

An embodiment of the invention are the compounds of formula I, wherein
$R^1$ is (C$_1$-C$_3$)alkyl;
V is phenylene;
Y -alkylene-O—;
W is a phenyl group,
   which is substituted one to three, preferably one or two, times by alkyl, halogen, —O-alkyl, —S(O)$_2$-alkyl, —NH(alkyl) or —N(alkyl)$_2$; preferably by alkyl,
   and wherein the alkyl group may be optionally substituted with one or several halogen atoms, preferably with chlorine and fluorine, especially with fluorine.

An embodiment of the invention are the compounds of formula I, wherein
$R^1$ is (C$_1$-C$_3$)alkyl;
V is phenylene;
Y -alkylene-NH—;
W is a phenyl group,
   which is substituted one to three, preferably one or two, times by alkyl, halogen, —O-alkyl, —S(O)$_2$-alkyl, —NH(alkyl) or —N(alkyl)$_2$; preferably by alkyl,
   and wherein the alkyl group may be optionally substituted with one or several halogen atoms, preferably with chlorine and fluorine, especially with fluorine.

An embodiment of the invention are the compounds according to formula I-a, wherein

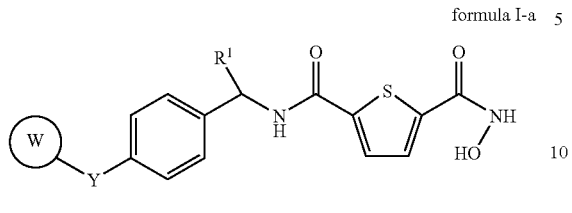

formula I-a wherein
R¹ is alkyl, which is optionally substituted one or several times by halogen;
Y —O—;
—O—CHR²;
-alkylene-O—;
-alkylene-O—CHR²—;
—NH—;
—NH—CHR²—;
-alkylene-NH—;
-alkylene-NH—CHR²—; or
-alkenylene-;
R² is alkyl or hydrogen;
W is a saturated carbocyclic group;
a saturated heterocyclic group;
a heteroaryl group; or
a substituted phenyl group;
and all pharmaceutically acceptable salts thereof.

An embodiment of the invention are the compounds according to formula I-aa, wherein

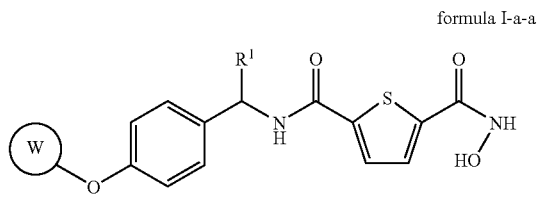

formula I-a-a wherein
R¹ is alkyl, which is optionally substituted one or several times by halogen;
W is a saturated carbocyclic group;
a saturated heterocyclic group;
a heteroaryl group; or
a substituted phenyl group;
and all pharmaceutically acceptable salts thereof.

An embodiment of the invention are the compounds of formula I-a-a, wherein
W is a saturated carbocyclic group.

An embodiment of the invention are the compounds of formula I-a-a, wherein
W is a saturated heterocyclic group.

An embodiment of the invention are the compounds of formula I-a-a, wherein
W is a heteroaryl group.

An embodiment of the invention are the compounds of formula I-a-a, wherein
W is a substituted phenyl group.

An embodiment of the invention are the compounds of formula I-a-b

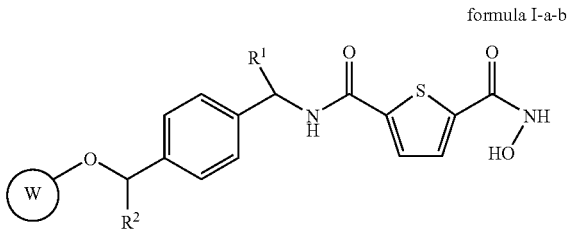

formula I-a-b wherein
R¹ is alkyl, which is optionally substituted one or several times by halogen;
R² is alkyl or hydrogen;
W is a saturated carbocyclic group;
a saturated heterocyclic group;
a heteroaryl group; or
a substituted phenyl group;
and all pharmaceutically acceptable salts thereof.

An embodiment of the invention are the compounds of formula I-a-b, wherein
W is a saturated carbocyclic group.

An embodiment of the invention are the compounds of formula I-a-b, wherein
W is a saturated heterocyclic group.

An embodiment of the invention are the compounds of formula I-a-b, wherein
W is a heteroaryl group.

An embodiment of the invention are the compounds of formula I-a-b, wherein
W is a substituted phenyl group.

An embodiment of the invention are the compounds of formula I-a-c

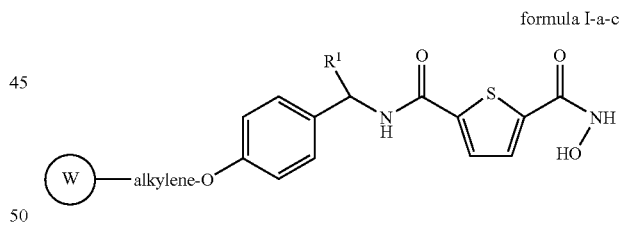

formula I-a-c wherein
R¹ is alkyl, which is optionally substituted one or several times by halogen;
W is a saturated carbocyclic group;
a saturated heterocyclic group;
a heteroaryl group; or
a substituted phenyl group;
and all pharmaceutically acceptable salts thereof.

An embodiment of the invention are the compounds of formula I-a-c, wherein
W is a saturated carbocyclic group.

An embodiment of the invention are the compounds of formula I-a-c, wherein
W is a saturated heterocyclic group.

An embodiment of the invention are the compounds of formula I-a-c, wherein
W is a heteroaryl group.
An embodiment of the invention are the compounds of formula I-a-c, wherein
W is a substituted phenyl group.
An embodiment of the invention are the compounds of formula I-a-d

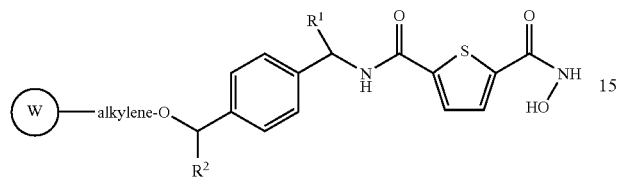

formula I-a-d wherein
R¹ is alkyl, which is optionally substituted one or several times by halogen;
R² is alkyl or hydrogen;
W is a saturated carbocyclic group;
a saturated heterocyclic group;
a heteroaryl group; or
a substituted phenyl group;
and all pharmaceutically acceptable salts thereof.
An embodiment of the invention are the compounds of formula I-a-d, wherein
W is a saturated carbocyclic group.
An embodiment of the invention are the compounds of formula I-a-d, wherein
W is a saturated heterocyclic group.
An embodiment of the invention are the compounds of formula I-a-d, wherein
W is a heteroaryl group.
An embodiment of the invention are the compounds of formula I-a-d, wherein
W is a substituted phenyl group.
An embodiment of the invention are the compounds of formula I-a-e

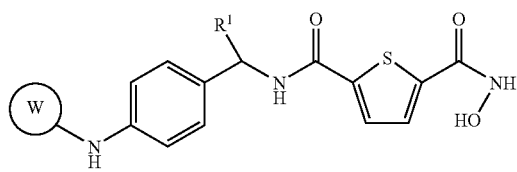

formula I-a-e wherein
R¹ is alkyl, which is optionally substituted one or several times by halogen;
W is a saturated carbocyclic group;
a saturated heterocyclic group;
a heteroaryl group; or
a substituted phenyl group;
and all pharmaceutically acceptable salts thereof.
An embodiment of the invention are the compounds of formula I-a-e, wherein
W is a saturated carbocyclic group.

An embodiment of the invention are the compounds of formula I-a-e, wherein
W is a saturated heterocyclic group.
An embodiment of the invention are the compounds of formula I-a-e, wherein
W is a heteroaryl group.
An embodiment of the invention are the compounds of formula I-a-e, wherein
W is a substituted phenyl group.
An embodiment of the invention are the compounds of formula I-a-f

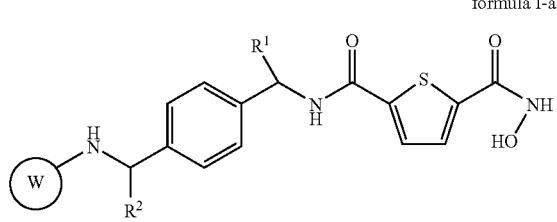

formula I-a-f wherein
R¹ is alkyl, which is optionally substituted one or several times by halogen;
R² is alkyl or hydrogen;
W is a saturated carbocyclic group;
a saturated heterocyclic group;
a heteroaryl group; or
a substituted phenyl group;
and all pharmaceutically acceptable salts thereof.
An embodiment of the invention are the compounds of formula I-a-f, wherein
W is a saturated carbocyclic group.
An embodiment of the invention are the compounds of formula I-a-f, wherein
W is a saturated heterocyclic group.
An embodiment of the invention are the compounds of formula I-a-f, wherein
W is a heteroaryl group.
An embodiment of the invention are the compounds of formula I-a-f, wherein
W is a substituted phenyl group.
An embodiment of the invention are the compounds of formula I-a-g

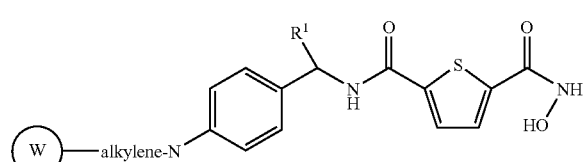

formula I-a-g wherein
R¹ is alkyl, which is optionally substituted one or several times by halogen;
W is a saturated carbocyclic group;
a saturated heterocyclic group;
a heteroaryl group; or
a substituted phenyl group;
and all pharmaceutically acceptable salts thereof.

An embodiment of the invention are the compounds of formula I-a-g, wherein
W is a saturated carbocyclic group.
An embodiment of the invention are the compounds of formula I-a-g, wherein
W is a saturated heterocyclic group.
An embodiment of the invention are the compounds of formula I-a-g, wherein
W is a heteroaryl group.
An embodiment of the invention are the compounds of formula I-a-g, wherein
W is a substituted phenyl group.
An embodiment of the invention are the compounds of formula I-a-h

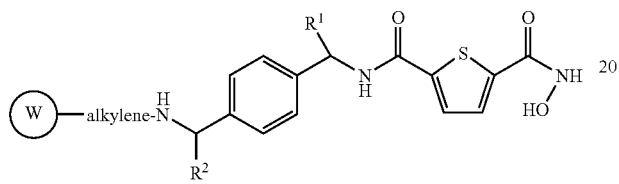

formula I-a-h wherein
R¹ is alkyl, which is optionally substituted one or several times by halogen;
R² is alkyl or hydrogen;
W is a saturated carbocyclic group;
    a saturated heterocyclic group;
    a heteroaryl group; or
    a substituted phenyl group;
and all pharmaceutically acceptable salts thereof.
An embodiment of the invention are the compounds of formula I-a-h, wherein
W is a saturated carbocyclic group.
An embodiment of the invention are the compounds of formula I-a-h, wherein
W is a saturated heterocyclic group.
An embodiment of the invention are the compounds of formula I-a-h, wherein
W is a heteroaryl group.
An embodiment of the invention are the compounds of formula I-a-h, wherein
W is a substituted phenyl group.
An embodiment of the invention are the compounds of formula I-a-i

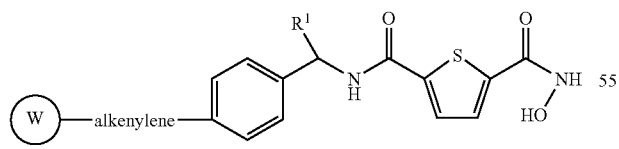

formula I-a-i wherein
R¹ is alkyl, which is optionally substituted one or several times by halogen;
W is a saturated carbocyclic group;
    a saturated heterocyclic group;
    a heteroaryl group; or
    a substituted phenyl group;
and all pharmaceutically acceptable salts thereof.

An embodiment of the invention are the compounds of formula I-a-i, wherein
W is a saturated carbocyclic group.
An embodiment of the invention are the compounds of formula I-a-i, wherein
W is a saturated heterocyclic group.
An embodiment of the invention are the compounds of formula I-a-i, wherein
W is a heteroaryl group.
An embodiment of the invention are the compounds of formula I-a-i, wherein
W is a substituted phenyl group.
An embodiment of the invention are the compounds of formula I-b

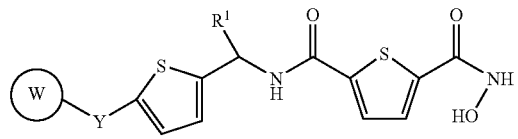

formula I-b wherein
R¹ is alkyl, which is optionally substituted one or several times by halogen;
Y —O—;
    —O—CHR²;
    -alkylene-O—;
    -alkylene-O—CHR²—;
    —NH—;
    —NH—CHR²—;
    -alkylene-NH—;
    -alkylene-NH—CHR²—; or
    -alkenylene-;
R² is alkyl or hydrogen;
W is a saturated carbocyclic group;
    a saturated heterocyclic group;
    a heteroaryl group; or
    a substituted phenyl group;
and all pharmaceutically acceptable salts thereof.
An embodiment of the invention are the compounds of formula I-b-a

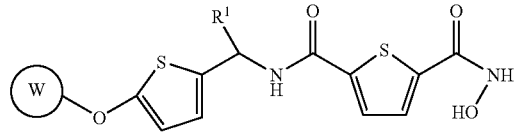

formula I-b-a wherein
R¹ is alkyl, which is optionally substituted one or several times by halogen;
W is a saturated carbocyclic group;
    a saturated heterocyclic group;
    a heteroaryl group; or
    a substituted phenyl group;
and all pharmaceutically acceptable salts thereof.

An embodiment of the invention are the compounds of formula I-b-a, wherein
W is a saturated carbocyclic group.
An embodiment of the invention are the compounds of formula I-b-a, wherein
W is a saturated heterocyclic group.
An embodiment of the invention are the compounds of formula I-b-a, wherein
W is a heteroaryl group.
An embodiment of the invention are the compounds of formula I-b-a, wherein
W is a substituted phenyl group.
An embodiment of the invention are the compounds of formula I-b-b

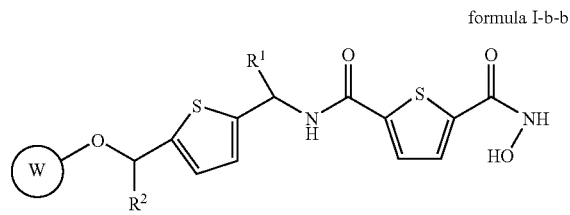

formula I-b-b wherein
R¹ is alkyl, which is optionally substituted one or several times by halogen;
R² is alkyl or hydrogen;
W is a saturated carbocyclic group;
   a saturated heterocyclic group;
   a heteroaryl group; or
   a substituted phenyl group;
and all pharmaceutically acceptable salts thereof.
An embodiment of the invention are the compounds of formula I-b-b, wherein
W is a saturated carbocyclic group.
An embodiment of the invention are the compounds of formula I-b-b, wherein
W is a saturated heterocyclic group.
An embodiment of the invention are the compounds of formula I-b-b, wherein
W is a heteroaryl group.
An embodiment of the invention are the compounds of formula I-b-b, wherein
W is a substituted phenyl group.
An embodiment of the invention are the compounds of formula I-b-c

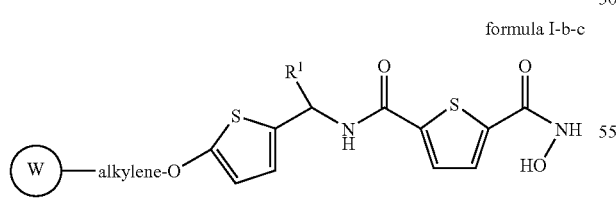

formula I-b-c wherein
R¹ is alkyl, which is optionally substituted one or several times by halogen;
W is a saturated carbocyclic group;
   a saturated heterocyclic group;
   a heteroaryl group; or
   a substituted phenyl group;
and all pharmaceutically acceptable salts thereof.

An embodiment of the invention are the compounds of formula I-b-c, wherein
W is a saturated carbocyclic group.
An embodiment of the invention are the compounds of formula I-b-c, wherein
W is a saturated heterocyclic group.
An embodiment of the invention are the compounds of formula I-b-c, wherein
W is a heteroaryl group.
An embodiment of the invention are the compounds of formula I-b-c, wherein
W is a substituted phenyl group.
An embodiment of the invention are the compounds of formula I-b-d

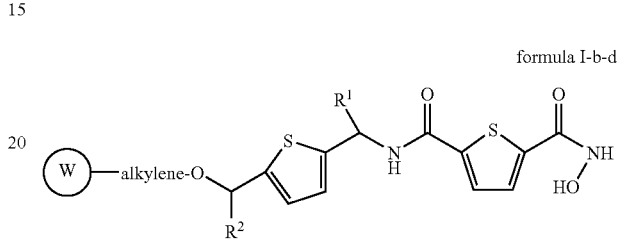

formula I-b-d wherein
R¹ is alkyl, which is optionally substituted one or several times by halogen;
R² is alkyl or hydrogen;
W is a saturated carbocyclic group;
   a saturated heterocyclic group;
   a heteroaryl group; or
   a substituted phenyl group;
and all pharmaceutically acceptable salts thereof.
An embodiment of the invention are the compounds of formula I-b-d, wherein
W is a saturated carbocyclic group.
An embodiment of the invention are the compounds of formula I-b-d, wherein
W is a saturated heterocyclic group.
An embodiment of the invention are the compounds of formula I-b-d, wherein
W is a heteroaryl group.
An embodiment of the invention are the compounds of formula I-b-d, wherein
W is a substituted phenyl group.
An embodiment of the invention are the compounds of formula I-b-e

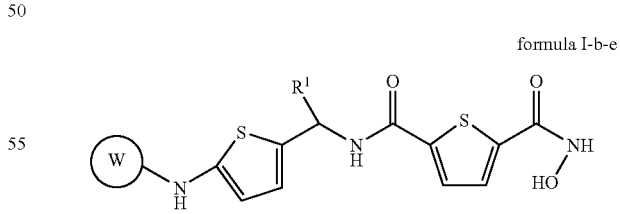

formula I-b-e wherein
R¹ is alkyl, which is optionally substituted one or several times by halogen;
W is a saturated carbocyclic group;
   a saturated heterocyclic group;
   a heteroaryl group; or
   a substituted phenyl group;
and all pharmaceutically acceptable salts thereof.

An embodiment of the invention are the compounds of formula I-b-e, wherein
W is a saturated carbocyclic group.
An embodiment of the invention are the compounds of formula I-b-e, wherein
W is a saturated heterocyclic group.
An embodiment of the invention are the compounds of formula I-b-e, wherein
W is a heteroaryl group.
An embodiment of the invention are the compounds of formula I-b-e, wherein
W is a substituted phenyl group.
An embodiment of the invention are the compounds of formula I-b-f

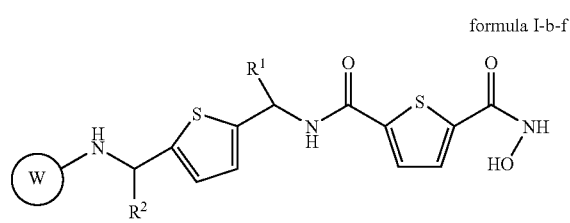

formula I-b-f wherein
R$^1$ is alkyl, which is optionally substituted one or several times by halogen;
R$^2$ is alkyl or hydrogen;
W is a saturated carbocyclic group;
a saturated heterocyclic group;
a heteroaryl group; or
a substituted phenyl group;
and all pharmaceutically acceptable salts thereof.
An embodiment of the invention are the compounds of formula I-b-f, wherein
W is a saturated carbocyclic group.
An embodiment of the invention are the compounds of formula I-b-f, wherein
W is a saturated heterocyclic group.
An embodiment of the invention are the compounds of formula I-b-f, wherein
W is a heteroaryl group.
An embodiment of the invention are the compounds of formula I-b-f, wherein
W is a substituted phenyl group.
An embodiment of the invention are the compounds of formula I-b-g

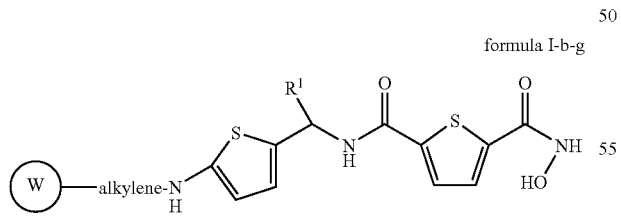

formula I-b-g wherein
R$^1$ is alkyl, which is optionally substituted one or several times by halogen;
W is a saturated carbocylic group;
a saturated heterocyclic group;
a heteroaryl group; or
a substituted phenyl group;
and all pharmaceutically acceptable salts thereof.

An embodiment of the invention are the compounds of formula I-b-g, wherein
W is a saturated carbocyclic group.
An embodiment of the invention are the compounds of formula I-b-g, wherein
W is a saturated heterocyclic group.
An embodiment of the invention are the compounds of formula I-b-g, wherein
W is a heteroaryl group.
An embodiment of the invention are the compounds of formula I-b-g, wherein
W is a substituted phenyl group.
An embodiment of the invention are the compounds of formula I-b-h

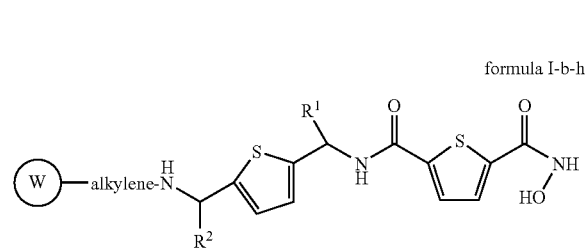

formula I-b-h wherein
R$^1$ is alkyl, which is optionally substituted one or several times by halogen;
R$^2$ is alkyl or hydrogen;
W is a saturated carbocyclic group;
a saturated heterocyclic group;
a heteroaryl group; or
a substituted phenyl group;
and all pharmaceutically acceptable salts thereof.
An embodiment of the invention are the compounds of formula I-b-h, wherein
W is a saturated carbocyclic group.
An embodiment of the invention are the compounds of formula I-b-h, wherein
W is a saturated heterocyclic group.
An embodiment of the invention are the compounds of formula I-b-h, wherein
W is a heteroaryl group.
An embodiment of the invention are the compounds of formula I-b-h, wherein
W is a substituted phenyl group.

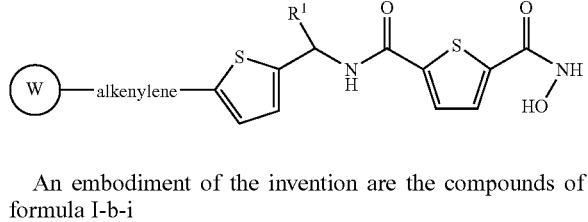

An embodiment of the invention are the compounds of formula I-b-i
formula I-b-i
wherein
R$^1$ is alkyl, which is optionally substituted one or several times by halogen;
W is a saturated carbocylic group;
a saturated heterocyclic group;
a heteroaryl group; or
a substituted phenyl group;
and all pharmaceutically acceptable salts thereof.

An embodiment of the invention are the compounds of formula I-b-i, wherein
W is a saturated carbocyclic group.
An embodiment of the invention are the compounds of formula I-b-i, wherein
W is a saturated heterocyclic group.
An embodiment of the invention are the compounds of formula I-b-i, wherein
W is a heteroaryl group.
An embodiment of the invention are the compounds of formula I-b-i, wherein
W is a substituted phenyl group.

Yet another embodiment of the invention is the process for the manufacture of the compounds of formula I, especially their (R)- and (S) enantiomers, by reacting a compound of formula IV

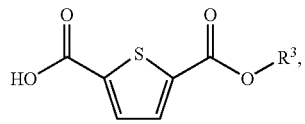

formula IV wherein
R³ is an alkyl group;
with an racemic, or (R)- or (S)-amine of the formula X

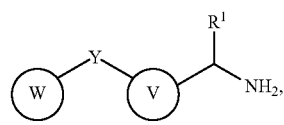

formula X wherein
V, W, Y and R¹ have the meaning given hereinabove for formula I,
in the presence of a suitable activating agent,
to give a compound of formula XI

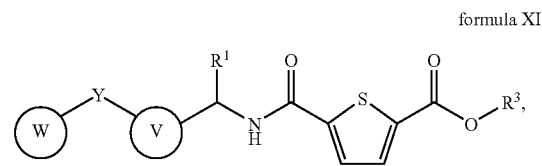

formula XI which is treated with hydroxylamine to give the respective compound of formula I; and
if desired, transforming said compound into its pharmaceutically acceptable salt.

The compounds of formula I, or a pharmaceutically acceptable salt thereof, which are subject of the present invention may be prepared by any process known to be applicable to the preparation of chemically-related compounds. Such processes, when used to prepare a thiophene hydroxamic acid derivative of the formula I, or a pharmaceutically-acceptable salt thereof, are illustrated by the following representative schemes and examples in which, unless otherwise stated, W, Y, V and R¹ have any of the meanings defined hereinbefore. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Depending on the nature of the linker Y, the compounds of formula I or formula XI can be prepared by different synthetic pathways. In the following schemes A to E and the corresponding descriptions some of the reaction sequences are illustrated.

A)
Compounds of the formulas I and XI wherein Y is -alkylene-NH—, -alkylene-O—, —O-alkylene-, —NH— or —O— and W, V, R¹ and R³ are as defined for formula I, can be prepared according to scheme A and are named XI-A and I-A. In the following scheme A several methods for the manufacture of the compounds of formulas I or I-A are illustrated:

Scheme A

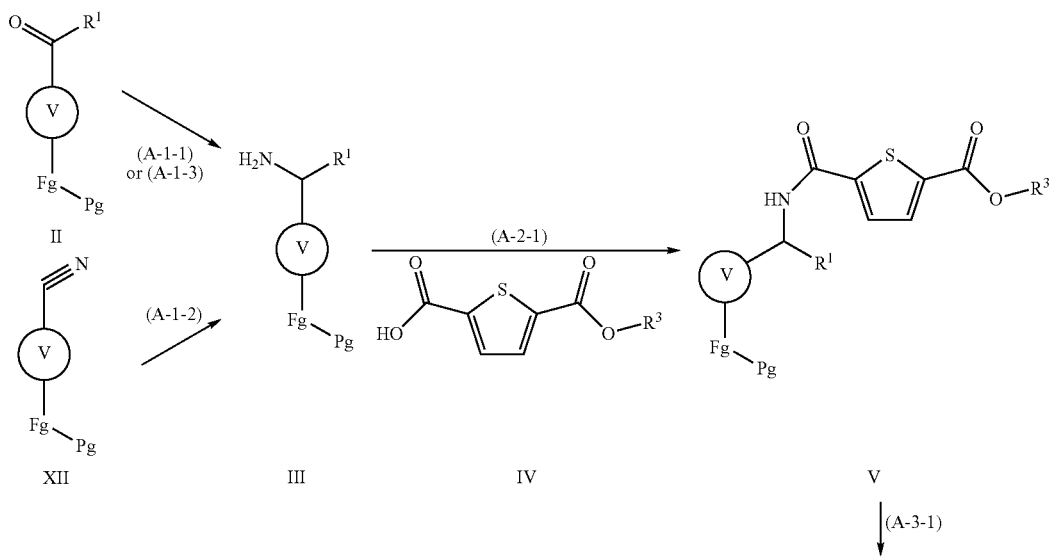

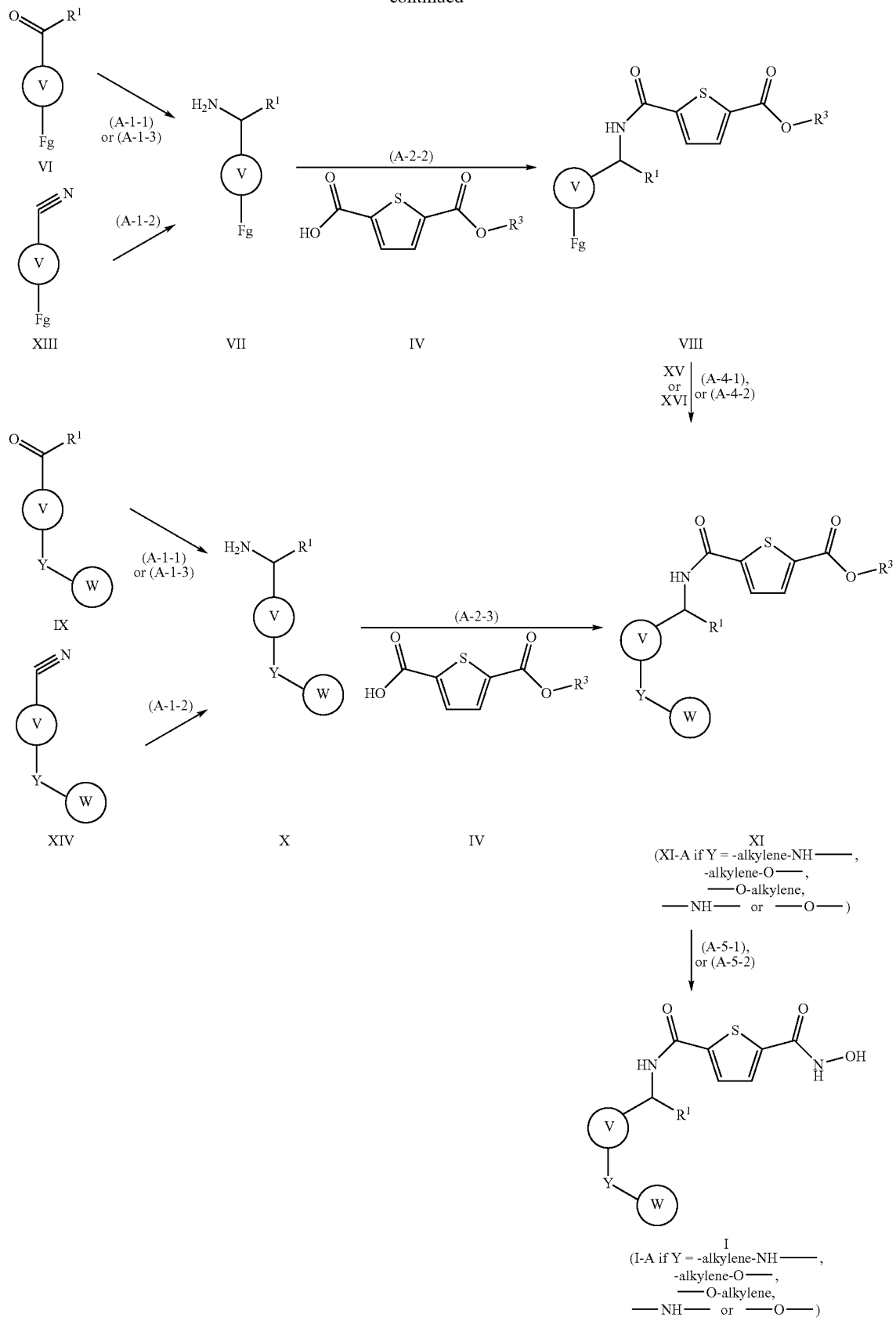

In scheme A, V, W and $R^1$ are defined as for formula I and $R^3$ is alkyl or optionally substituted benzyl. Fg means a functional group suitable for metal catalyzed (cross-) coupling reactions like e.g. fluoride, iodide, bromide, chloride, triflate, boronic acids, boronic acid pinacolesters or trialkylstannanes (e.g. $Me_3Sn$, $Bu_3Sn$) or other suitable functional groups. Pg means a protecting group like e.g. benzyl-, p-methoxybenzyl-, tert-butyloxycarbonyl-, trityl-, or silyl groups such as the trimethylsilyl- or dimethyl-tert-butylsilyl group or other suitable protecting groups.

(A-1-1) Some of the amines of the general formulas III, VII or X, wherein W, Y, V, Fg and Pg are defined as hereinbefore, are commercially available. They can also be prepared for example by reductive amination from the corresponding ketones of general formulas II, VI or IX.

This reaction is typically carried out as a one-pot reaction with the formation of the imine and its subsequent reduction to the amine taking place in the same reaction vessel. The reaction mixture usually contains a source of ammonia for example $NH_4OAc$ and a reducing agent for example sodium cyanoborohydride and is heated in a suitable solvent e.g. methanol.

(A-1-2) Another method for the preparation of amines of general formulas III, VII or X is the addition of a Grignard reagent $R^1$—MgBr or an organolithium compounds Li—$R^1$ with $R^1$ as defined hereinbefore to an aromatic nitrile of the general formulas XII, XIII or XIV wherein W, Y, V, Fg and Pg are defined as hereinbefore and subsequent reduction of the imine (Synth. Commun. 1998, 28(21), 4067).

Pure (R) and (S) enantiomers of amines of the formulas III, VII or X in which W, Y, V, $R^1$, Pg and Fg have the meaning defined hereinbefore are commercially available or can be prepared from commercially available, optional enantiomerically pure precursors by standard procedures of organic chemistry.

(A-1-3) A method to introduce the chiral center of formulas III, VII or X is for example the enantioselective reduction of the corresponding arylalkylketone of formulas II, VI or IX. This can be accomplished e.g. with a combination of the chiral CBS (Corey, Bakshi, Shibata) reagent and the borane-THF complex, the borane-diethylaniline complex or the borane-dimethylsulfide as the reducing agent (Corey, E. J., et al., Angew. Chemie 110 (1998) 2092-2118). Yet another method for the enantioselective reduction of the arylalkylketone of formulas II, VI or IX employs diisopinocampheylchloroborane in a suitable solvent e.g. THF and subsequent work up with e.g. $H_2O_2/NaHCO_3$ or diethanolamine (Brown, H. C., et al., J. Am. Chem. Soc. 110 (1988) 1539-1546; Wiegers, A., and Scharf, H.-D., Tetr. Asym. 7 (1996) 2303-2312). Another method is the asymmetric catalytic hydrogenation of the arylalkylketone of formulas II, VI or IX in the presence of transition metal catalyst with chiral ligands of Noyori type (Noyori, R., et al., Angew. Chem. 113 (2001) 40-75). The chiral alcohols that are obtained in these enantioselective reductions of the arylalkylketone of formulas II, VI or IX can then be converted to the amines of formulas III, VII or X by standard procedures of synthetic chemistry as described e.g. in Chen, C.-P., et al., Tetrahedron Lett. 32 (1991) 7175-7178: displacement of the hydroxy group with a nitrogen functionality (for example with azide or with phthalimide) under Mitsunobu conditions (Mitsunobu, O., Synthesis 1 (1981) 1-28) and subsequent conversion to the amine (e.g. reduction of the azide with triphenylphosphine or catalytic hydrogenation (Pd/C, $H_2$, $CF_3COOH$) or hydrazinolysis of the phthalimide).

(A-1-4) Another method for the asymmetric preparation of 1-(aryl)ethylamines is the nucleophilic addition of methyl lithium to chiral oxime ethers (Yamazaki, N., et al., Tetrahedron Lett. 42 (2001) 5029-5032) and subsequent conversion to the amine.

(A-1-5) Racemic amines of the of formulas III, VII or X in which W, Y, V, $R^1$, Pg and Fg have the meaning defined hereinbefore can be separated into their enantiomers by known procedures as, for example, fractional crystallization of the diastereomeric salts that are formed with suitable chiral enantiomerically pure acids (Smith, H. E., et al., J. Am. Chem. Soc. 105 (1983) 1578-1584; U.S. Pat. No. 4,983,771). These acids may be commercially available, e.g. mandelic acid, tartaric acid, lactic acid, camphoric acid, camphorsulfonic acid, N-acetylleucine, dibenzoyltartaric acid or they are especially designed for the resolution of 1-arylethylamines for example 2-naphtylglycolic acid (Kinbara, K., et al., J. Chem. Soc., Perkin Trans. 2 (2000) 1339-1348) or isopropylidene glycerol 3-carboxy-2-naphtoate (Pallavicini, M., Tetr. Asym. 12 (2001) 2489-2495).

(A-1-6) Another method for the separation of the two enantiomers of racemic amines of formulas III, VII or X is the enzyme catalyzed resolution, for example with lipase from *candida Antarctica* B (Rasor, J. P., and Voss, E., Applied Catalysis A: General 221 (2001) 145-158; Iglesias, L. E., et al., Tetr. Asym. 8 (1997) 2675-2677)

(A-2-1) Compounds of formula V, wherein Pg, Fg, V and $R^1$ have the meaning defined hereinbefore, are prepared from compounds of the formula IV, wherein $R^3$ is a ($C_1$-$C_4$)alkyl group, preferably a methyl, ethyl or tert-butyl group or optionally substituted benzyl, with an amine of formula III.

This reaction typically involves a two-step one-pot procedure.

In the first step, the carboxylic acid of the formula IV becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester formed by the reaction of the acid and a phenol such as pentafluorophenol; an active ester formed by the reaction of the acid and N-hydroxybenzotriazole; the corresponding carbonylimidazole of compounds of formula IV formed by the reaction of the acid and N,N'-carbonyldiimidazole; an acyl azide formed by the reaction of the acid and an azide such as diphenylphosphoryl azide; an acyl cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conventionally at or below 0° C.

In the second step, an amine of the formula III, in which V, Fg, Pg and $R^1$ have the meaning defined hereinbefore is added to the solution, at the temperature used for the activation, and the temperature is slowly adjusted to ambient temperature. An appropriate scavenger base like e.g. triethylamine, or diisopropylethylamine may be added to the reaction mixture. These methods are well known to those skilled in the art. In principle, all methods for the synthesis of amides as used in peptide chemistry as described in e.g. Houben-Weyl, "Methoden der organischen Chemie", Vols. XV/1 and XV/2, Georg Thieme Verlag, Stuttgart, are also applicable. Compounds of formula IV are described in the literature as for example in U.S. Pat. No. 2,680,731 and Gaddard, C. J. et al., J. Heterocycl. Chem. 28 (1991) 17. These monoesters are usually prepared by selective saponification of the diester or oxidation of the corresponding aldehyde, but other methods may be useful as well and are well known to those skilled in the art.

(A-2-2) Analogously the compounds of formula VIII, wherein V, $R^1$, $R^3$ and Fg are defined as hereinbefore can be obtained by the reaction of compounds of formula IV with an amine of the formula VII, wherein Fg, V and $R^1$ have the meaning defined hereinbefore.

The reaction can be carried out under conditions as described for the preparation of compounds of formula II in section (A-2-1).

(A-2-3) In an analogous manner compounds of formula XI, wherein W, Y V, $R^1$ are $R^3$ defined as hereinbefore, can be obtained by the reaction of compounds of formula IV with an amine of the formula X, wherein W, Y, V and $R^1$ have the meaning defined hereinbefore.

The reaction can be carried out under conditions as described for the preparation of compounds of formula II in section (A-2-1).

(A-3-1) After the amide formation reaction (A-2-1) the functional group Fg in formula V bears a suitable protecting group Pg which is liberated to give compounds of formula VIII. The deprotection reaction applied depend on the type of the protecting group.

(A-4-1) Compounds of the formula XI wherein Y is -alkylene-NH— or —NH— and W, V, $R^1$, $R^3$ as defined for formula I, can be prepared by a palladium catalyzed cross coupling reaction between compounds of formula VIII and a compound of formula XV,

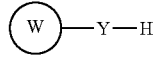

XV wherein W and Y have the meaning defined hereinbefore.

This reaction may be for example, but is not limited to, of Buchwald-Hartwig type and related reactions (Fg is iodide, bromide, triflate or chloride; see e.g. Kwong, F. Y., Org. Lett. 4 (2002) 581-548; Louie, J., et al., J. Org. Chem. 62 (1997) 1268-1273; Wolfe, J. P., et al., J. Am. Chem. Soc. 119 (1997) 6054-6058; Yin, J. et al., Org. Lett. 4 (2002) 3481-3484; Mann, G., et al., J. Am. Chem. Soc. 120 (1998) 827-828).

Another method is a palladium catalyzed cross coupling reaction between compounds of formula XV and an arylboronic acid of formula VIII wherein Fg is $B(OH)_2$ (see e.g. Chan, D. T. M., et al., Tetrahedron Lett. 39 (1998) 2933-2936; Lam, P. Y. S., et al., Tetrahedron Lett. 39 (1998) 2941-2944).

(A-4-2) Compounds of the formula XI wherein Y is —O—, -alkylene-O— or —O-alkylene- and W, V, $R^1$, $R^3$ as defined for formula I can be prepared by a coupling reaction between compounds of formula VIII and a compound of formula XVI,

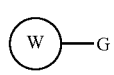

XVI wherein W has the meaning defined hereinbefore and G is a functional group (which is compatible to Fg) as defined herein below in this section.

This reaction may be for example, but is not limited to, of Ullmann type or the reaction may be palladium catalyzed or copper catalyzed (Fg is F, Br, I or OTf and G is —OH, -alkylene-OH; or Fg is —OH, -alkylene-OH and G is F, Br, I or OTf, see e.g. Yeager, G. W., et al., Synthesis 1 (1995) 28-30; Aranyos, A., et al. J. Am. Chem. Soc. 121 (1999) 4369-4378; Palucki, M., et al., J. Am. Chem. Soc. 119 (1997) 3395-3396; Marcoux, J.-F., et al., J. Am. Chem. Soc. 119 (1997) 10539-10540).

Another method is a copper catalyzed cross coupling reaction between compounds of formula XVI and compounds of formula VIII with Fg is $B(OH)_2$ and G is —OH, -allylene-OH or Fg is —OH, -alkylene-OH and G is $B(OH)_2$; see e.g. Evans, D. A., et al., Tetrahedron Lett. 39 (1998) 2937-2940).

(A-5-1) One method for the production of compounds of the formula I involves the reaction of compounds of the formula XI, wherein W, Y, V and $R^1$ have the meaning defined hereinbefore and $R^3$ is a $(C_1-C_4)$alkyl group, preferably a methyl, ethyl or tert-butyl group, or optionally substituted benzyl group, with hydroxylamine in the presence of a suitable base. The reaction is carried out in an inert solvent or diluent such as methanol or ethanol at temperatures between 0° C. and 100° C., conventionally at or near ambient temperature, and at a pH between 10 and 12. A suitable base is, for example, an alcoholate, e.g. sodium methylate. Instead of generating hydroxylamine in situ, it can be released separately and can be applied as a solution in an organic solvent, as for example an alcohol like methanol or ethanol.

(A-5-2) Another method for the preparation of compounds of the formula I is a reaction sequence via the carboxylic acids of formula XVII

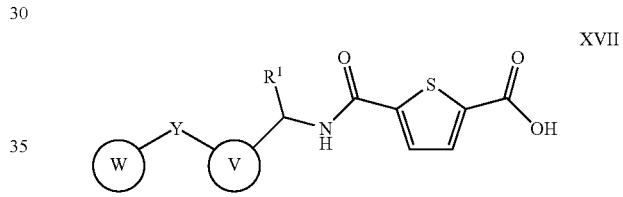

XVII wherein V, W, Y and $R^1$ have the meaning as defined hereinbefore.

These intermediates of formula XVII are prepared from compounds of the formula XI by hydrolysis. The conditions under which the hydrolysis is carried out depend on the nature of the group $R^3$. When $R^3$ is a methyl or ethyl group, the reaction is carried out in the presence of a base, for example, lithium hydroxide, sodium hydroxide, or potassium hydroxide in an inert solvent or diluent, for example, in methanol or ethanol. When $R^3$ is a tert-butyl group, the reaction is carried out in the presence of an acid, for example, a solution of hydrochloric acid in an inert solvent such as diethyl ether or dioxane, or trifluoroacetic acid in dichloromethane. When $R^3$ is a benzyl group, the reaction is carried out by hydrogenolysis in the presence of a noble metal catalyst such as palladium or platinum on a suitable carrier, such as activated carbon. Not necessarily all methods of hydrolysis are compatible with all groups Y or $R^1$. In cases where the features of these groups do not allow the usage of a certain method of hydrolysis, other methods of preparation need to be applied.

Compounds of formula XVII are new and also subject of the present invention.

Subsequent reaction of the acids of formula XVII with hydroxylamine yields the compounds of formula I. This reaction typically involves a two-step one-pot procedure.

In the first step, the carboxylic acid of the formula XVII becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conventionally at or below 0° C.

In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

In the following, further methods for the preparation of compounds of the general formula I are described which are not explicitly shown in scheme 1.

One alternative route for the preparation of compounds of the formula I is the introduction of O-protecting groups Q for the hydroxamic acid moiety of compounds of formula I and deprotection of the hydroxamate in the final reaction step to liberate compounds of formula I.

Suitable O-protecting groups Q may be benzyl-, p-methoxybenzyl-, tert-butyloxycarbonyl-, trityl-, or silyl groups such as the trimethylsilyl- or dimethyl-tert-butylsilyl-group.

To introduce these protecting groups into intermediates V or VIII, an analogous reaction route as described in section (A-5-2) can be chosen. The first step is the hydrolysis of those compounds to the corresponding carboxylic acids, which are activated and subsequently reacted with Q-O—$NH_2$ to the desired O-protected hydroxamates.

The final deprotection reactions applied depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert-butyloxycarbonyl-trityl-, or a silyl group such as the trimethylsilyl- or dimethyl-tert-butylsilyl-group, the reaction is carried out in the presence of acids at a temperature between −20° C. and 60° C., preferably between 0° C. and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert-butylsilyl group, the reaction can also be carried out in the presence of a fluoride source such as sodium fluoride or tetrabutyl ammonium fluoride in an inert solvent such as dichloromethane. Not necessarily all protecting groups Q are compatible with all groups Y, X and $R^1$. In cases where the features of these groups don't allow the usage of a certain protecting group, other protecting groups Q or other methods of preparation need to be applied.

Compounds of formula I can also be prepared with methods of solid phase supported synthesis. 2,5-thiophenedicarboxylic acid is reacted with a hydroxylamine moiety (—O—$NH_2$) bound to a resin, e.g. hydroxylamine Wang resin or hydroxylamine 2-chlorotrityl resin to form a resin-bound hydroxamic acid. The second carboxylic acid moiety is reacted with amines of formula III, VII, or X, wherein V, W, Y, and $R^1$ have the meaning defined hereinbefore and Fg represents a suitable functional group as described hereinbefore, by standard methods of amide bond formation as described in e.g. Houben-Weyl, "Methoden der organischen Chemie", Vols. XV/1 and XV/2. Optionally, the present protecting group Pg has to be cleaved, and ring W and linker Y having the meaning as described hereinbefore have to be introduced. This can be done as described in section (A-4-1) or (A-4-2). After this, the hydroxamic acid is liberated from the solid support. This can be done for example with TFA. Typically, the cleavage of the hydroxamic acids is achieved by treatment of the resin with 50% TFA in dichloromethane in the presence of triisopropyl silane at ambient temperature. The crude products can be purified by LC-MS, if necessary.

A method for the production of pure (R)- and (S)-enantiomers of formula I includes the employment of enantiomerically pure amines of formulas III, VII or X within the synthesis of the compounds of formula V, VIII, and XI as described in section (A-2-1) to (A-2-3).

Yet another method for the preparation of pure (R)- and (S)-enantiomers of compounds of formula I is the synthesis of racemic compounds according to methods (A-1-1) to (A-5-2), (B-1) to (B-6), (C-1) to (C-4), (D-1) to (D-5) or (E-1) to (E-5). The racemates can be separated subsequently into both enantiomers on either the stage of the final products or the precursors of formula XI. The separation can be performed by chromatography on an analytical, semipreparative or preparative scale using suitable optically active stationary phases with suitable eluents. Suitable optically active stationary phases include, but are not limited to, silica (e.g. ChiraSper, Merck; Chiralpak OT/OP, Baker), cellulose or amylose esters or carbamates (e.g. Chiralpak AD, Daicel Chemical Industries Ltd.; Chiracel OD-CSP, Daicel; Chiracel OB/OY, Baker) or others (e.g. Crownpak, Daicel or Chiracel OJ-R, Baker). Suitable eluents include, but are not limited to hexane, heptane, ethanol, isopropanol, acetonitrile, water and mixtures thereof. Other methods for the separation of enantiomers can also be applied, like the formation of diastereomeric compounds from compounds of the formula I together with other optically active compounds, e.g. camphorsulfonic acid or brucin, and separation of these diastereomeric compounds, followed by the liberation from the optically active agent.

Depending on the nature of the linker Y, the compounds of formula XI can be prepared by different synthetic pathways. Section A described the synthesis of compounds of the general formula IX-A with Y=-alkylene-NH—, -alkylene-O—, —O— alkylene, —NH— or —O—. In the following schemes B to E additional reaction sequences for the preparation of compounds XI with other linkers and the corresponding descriptions are illustrated.

B)

Compounds of the formula XI, wherein Y is -alkylene-NH—$CHR^2$— or —NH—$CHR^2$—, can be prepared according to scheme B and are named XI-B. In the following scheme B, the linker Y, which is -alkylene-NH—$CHR^2$— or —NH—$CHR^2$—, is represented by -T-NH—$CHR^2$—, wherein T means a single bond or alkylene as defined for formula I.

Scheme B

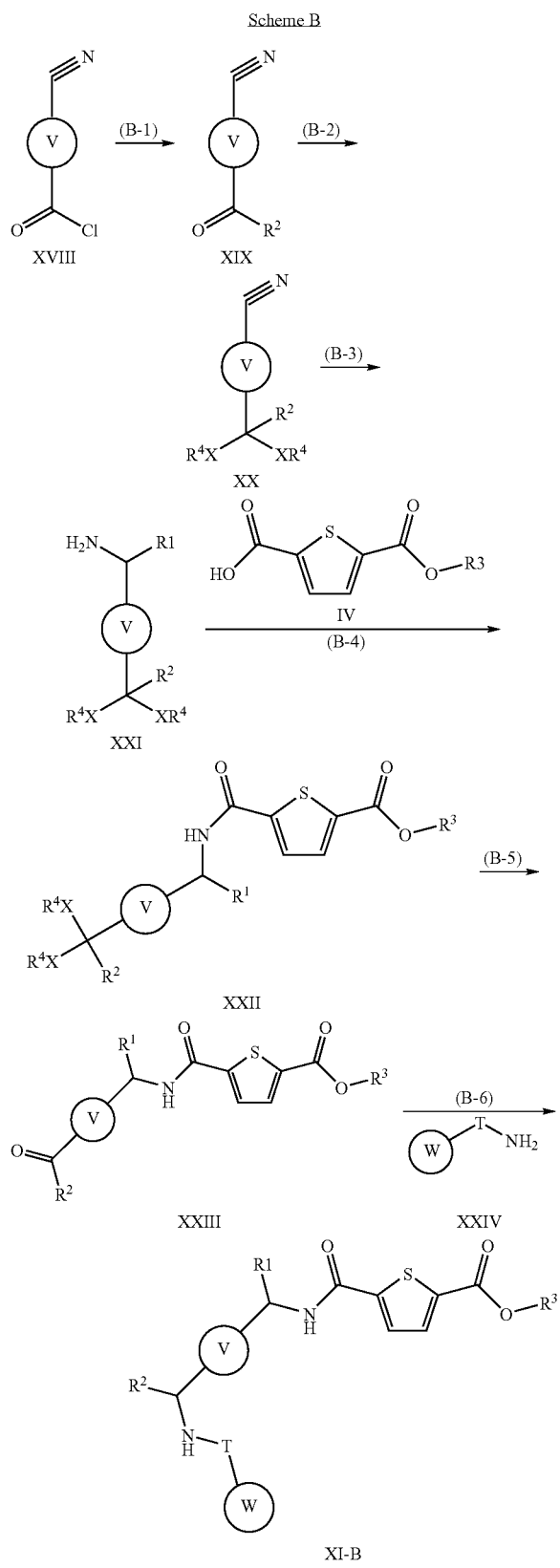

In scheme B, V, W, R¹ and R² are defined as for formula I and R³ is alkyl or optionally substituted benzyl. X is O or S and R⁴ is alkyl or both XR⁴ form an optionally substituted dioxolane, dioxane, dithiolane or dithiane ring. T is a single bond or alkylene (B-1) Nitriles of the general formula XIX, wherein ring V and R² have the meaning defined hereinbefore, are commercially available or they can be prepared by standard procedures of organic chemistry. One example is the addition of organocadmium R²$_2$Cd or lithium organocuprates LiCuR²$_2$, wherein R² has the meaning defined hereinbefore, to acyl halides of the general formula XVIII, wherein ring V has the meaning defined hereinbefore.

(B-2) The Fg protected nitrile of the formula XX (with X is O, S, and R⁴ is alkyl or both XR⁴ forming an optionally substituted dioxolane, dioxane, dithiolane or dithiane ring) can be prepared for example from nitriles of the general formula XIX (scheme B), wherein V has the meaning defined hereinbefore, by treating the carbonyl group e.g. with an alcohol or a diol like ethylene glycol or 1,3-propanediol or a thiol or a dithiol in the presence of an acid (toluene sulfonic acid, boron trifluoride etherate, HCl, pyridinium tosylate, acetic acid and the like) to give the nitriles of formula XX.

(B-3) Then the nitrile group is converted into an amine for example by addition of Grignard (R¹MgBr) or organolithium (R¹Li) compounds and subsequent hydrolysis to form the corresponding carbonyl compound which is subjected to reductive amination as described in (A-1-1) to form an amine of formula XXI.

(B-4) Compounds of the general formula XXII can be obtained by the reaction of compound IV with Fg protected amines of the formula XXI. The reaction can be carried out under conditions as described for the preparation of compounds of formula V in section (A-2-1).

(B-5) Compounds of the formula XXIII can be obtained from the functional group (Fg) protected compounds of formula XXII (with Pg-Fg- is (R⁴X)$_2$CR²—) with X is O, S, and R⁴ is alkyl or both XR⁴ forming an optionally substituted dioxolane, dioxane, dithiolane or dithiane ring) by acidic hydrolysis of the ketal (X is O) or by reaction with mercury (II) salts or oxidation of the thioketal (X is S).

(B-6) Compounds of formula XI-B can be prepared by reductive amination of a primary amine of the general formula XXIV, wherein T¹ means a bond or alkylene as defined hereinbefore, with a carbonyl compound of the general formula XXIII.

The condensation is typically achieved by heating the amine and the carbonyl compound in a suitable solvent like for example ethanol, methanol, acetonitrile or N,N-dimethylformamide (DMF) at temperatures between 20° C. and 150° C. Typical reducing agent for the subsequent reduction of the imine to the amine XI-B are e.g. sodium cyanoborohydride, sodium borohydride in suitable solvents like e.g. THF or methanol.

C)

Compounds of the formula XI wherein Y is -alkylene-NH— can be prepared according to scheme C and are named XI-C. In the following scheme C the linker Y, which is -alkylene-NH—, is represented by -T-CHR⁵—NH—, wherein T is a single bond or alkylene and R⁵ is alkyl, so that the resulting group -T-CHR⁵—NH— forms an -alkylene-NH— group as defined for formula I.

Scheme C

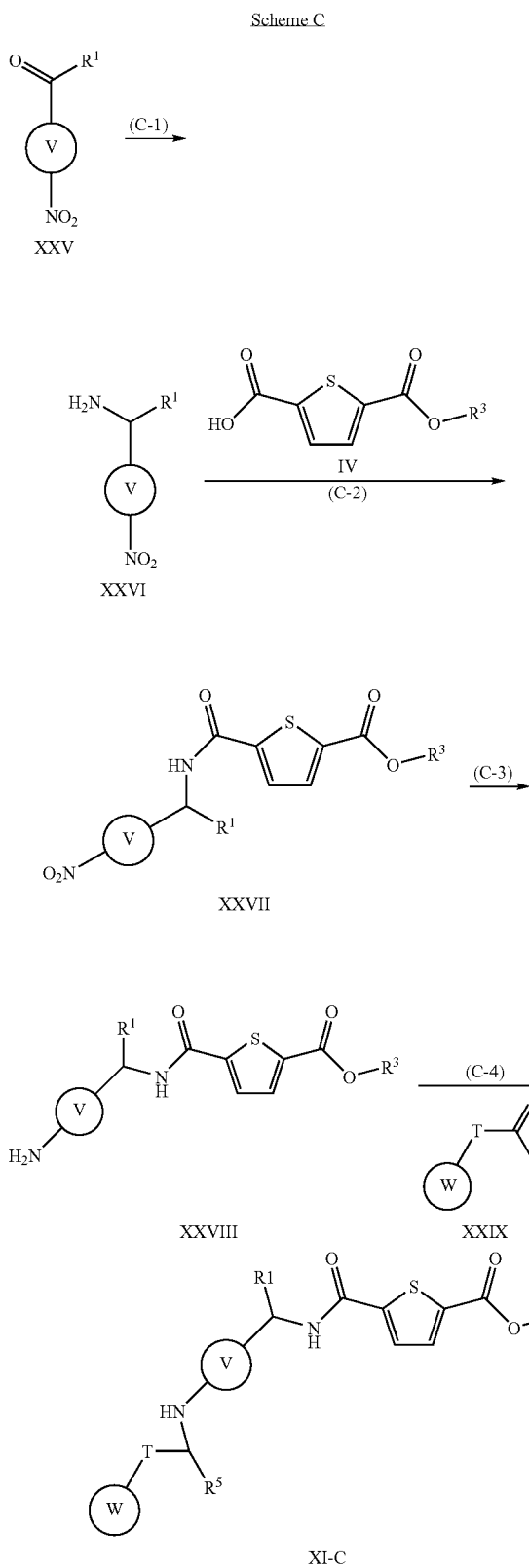

In scheme C, V, W and R¹ are defined as for formula I and R³ is alkyl or optionally substituted benzyl. R¹ is alkyl and T is a single bond or alkylene.

(C-1) The amine of the formula XXVI (comprising a nitro group as protecting group or precursor group for a further amino function) can be prepared for example from ketones of formula XXV, wherein V and R¹ have the meaning defined hereinbefore, by reductive amination as described in (A-1-1) yielding compounds of formula XXVI.

Instead of the nitro group, other suitable amino protecting groups or groups, which can be easily converted to an amino group after the reaction of XXVI with IV, might also be employed.

(C-2) Compounds of the general formula XXVII can be obtained by the reaction of compounds of formula IV with Fg protected amine of the formula XXVI (—NO₂ as amino protecting group). The reaction can be carried out under conditions as described for the preparation of compounds of formula V in section (A-2-1).

(C-3) Compounds of the formula XXVIII can be obtained from the Fg protected compounds of formula XXVII by reduction of the nitro group for example by catalytic hydrogenation or chemical reducing agents (e.g. $SnCl_2$, Fe, Zn) in acidic solution to form compounds XXVIII.

(C-4) Compounds of the formula XI-C can be prepared by reductive amination of a primary amine of the general formula XXVIII with a carbonyl compound of the general formula XXIX.

The reaction can be carried out under conditions as described for the preparation of compound XI-B in section (B-6).

D)

Compounds of the formula XI wherein Y is -alkylene-O—CHR²—, —O—CHR²—, -alkylene-O— or —O—, can be prepared according to schemes D-1 and D-2 and are named XI-D.

In the following scheme D-1 the linker Y, which is -alkylene-O—CHR²— or —O—CHR²—, is represented by -T-O—CHR²—, wherein T means a single bond or alkylene as defined hereinbefore.

Scheme D-1

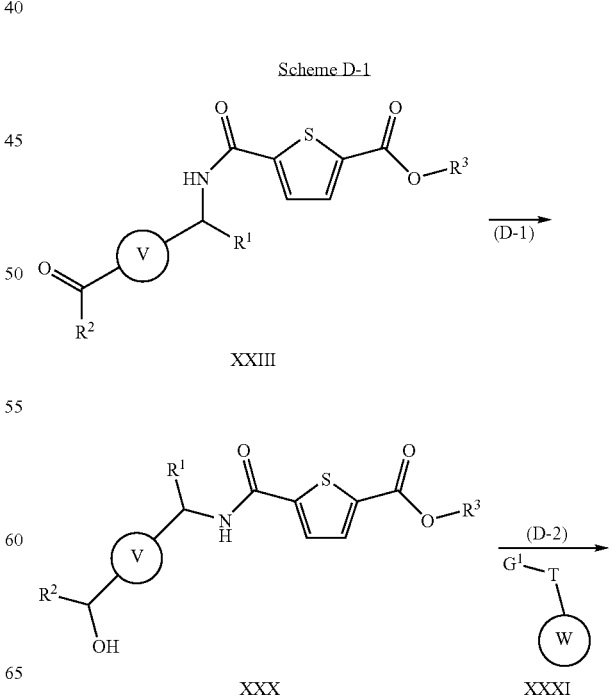

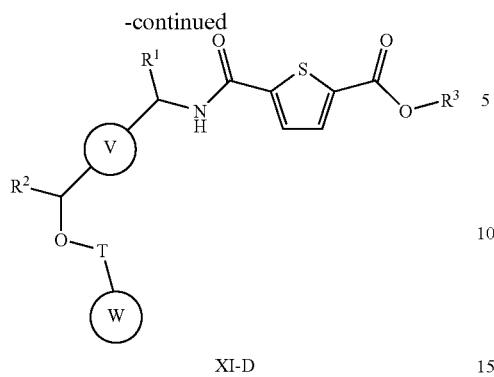

XI-D

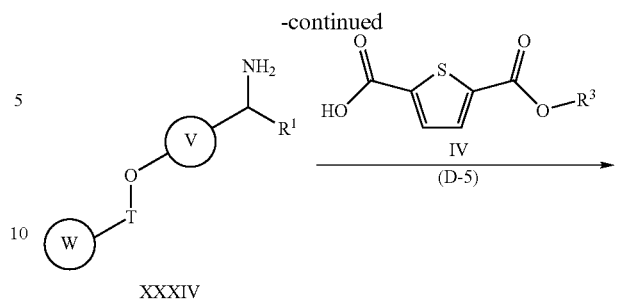

XXXIV

In scheme D-1, V, W, $R^1$ and $R^2$ are defined as for formula I and $R^3$ is alkyl or optionally substituted benzyl. $G^1$ is —Br, —I, —Cl, -tosylate, -mesylate and the like. T is a single bond or alkylene (D-1) Alcohols of the formula XXX can be prepared by reduction of compounds of formula XXIII e.g. with sodium borohydride or sodium cyanoborohydride.

(D-2) Compounds of formula XI-D can be prepared for example from alcohols of the general formula XXX by reaction with a compound of the general formula XXXI, wherein T means a single bond or alkylene as defined hereinbefore according to scheme D-2. If T means a single bond, W is selected from saturated cyclic groups or saturated heterocycles. If T means alkylene, W is defined as for formula I above. $G^1$ means a suitable leaving group, e.g. $G^1$ is —Br, —I, —Cl, -tosylate, -mesylate and the like. The reaction is carried out in the presence of a suitable base e.g. potassium carbonate, potassium hydroxide or sodium hydroxide and the like in a suitable solvent, e.g. THF, acetone, DMF or N,N-dimethylsulfoxide (DMSO).

In the following scheme D-2 the linkers Y, which is -alkylene-O— or —O—, is represented by -T-O—, wherein T means a single bond or alkylene as defined hereinbefore.

Scheme D-2

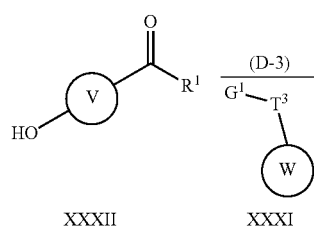

XXXII    XXXI

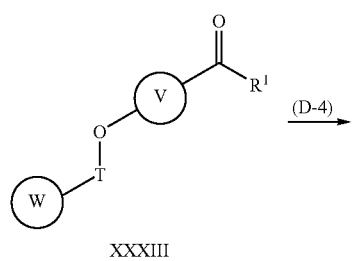

XXXIII

XI-D

In scheme D-2, V, W, $R^1$ and $R^2$ are defined as for formula I and $R^3$ is alkyl or optionally substituted benzyl. $G^1$ is —Br, —I, —Cl, -tosylate, -mesylate and the like. T is a single bond or alkylene (D-3) Ketones of the general formula XXXIII wherein Y is -alkylene-O— or —O— can be prepared for example from alcohols of the general formula XXXII wherein V and $R^1$ are defined as hereinbefore, by the reaction with a compound W-T-$G^1$ of the general formula XXXI wherein T means a bond or alkylene as defined hereinbefore. If T means a bond, W is selected from saturated cyclic groups or saturated heterocyclic groups. If T means alkylene, W is defined as for formula I above. $G^1$ means a suitable leaving group, e.g. $G^1$ is —Br, —I, —Cl, -tosylate, -mesylate and the like in the presence of a suitable base e.g. potassium carbonate, potassium hydroxide or sodium hydroxide and the like in a suitable solvent, e.g. THF, acetone, DMF or N,N-dimethylsulfoxide (DMSO).

(D-4) Amines of the general formula XXXIV can be prepared for example from ketones of the general formula XXXII wherein W, V, T, and $R^1$ are defined as hereinbefore by reductive amination as described in (A-1-1) to form compounds of formula XXXIV.

(D-5) Compounds of formula XI-D can be prepared for example by the reaction of compounds of formula IV with amines of the general formula XXXIV. The reaction can be carried out under conditions as described for the preparation of compounds of formula XI in section (A-2-3).

E)

Compounds of the formula XI wherein Y is -alkenylene- can be prepared according to scheme E and are named XI-E. In the following scheme E the linker Y, which is -alkenylene-, is represented by -T-$CR^6$=$CR^2$—, wherein T is a single bond or alkylene, and $R^2$ and $R^6$ are alkyl (or hydrogen), so that the resulting group -T-$CR^6$=$CR^2$— forms an alkenylene group as defined for formula I.

Scheme E

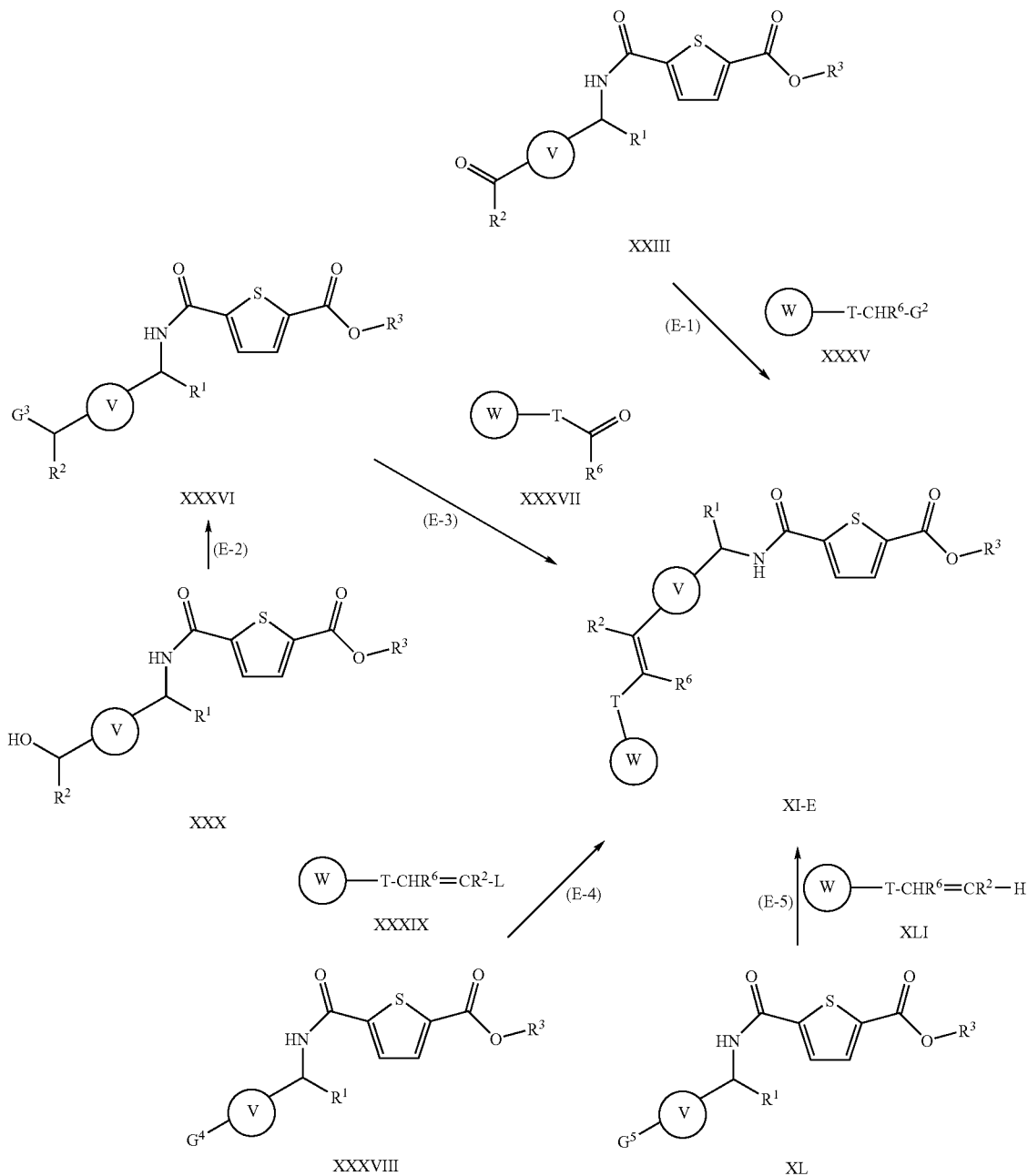

In scheme E, V, W, R¹ and R² are defined as for formula I, R³ is alkyl or optionally substituted benzyl and R⁶ is alkyl or hydrogen. T is a single bond or alkylene. G² is halide, especially —Br or —I. G³ is —Br or —I. G⁴ is halogen, especially Br, Cl or I. G⁵ is e.g. Br, I or OTf. L is a boronic acids, a boronic acid pinacolester and the like or a trialkylstannane (e.g. Me₃Sn, Bu₃Sn).

(E-1) Compounds of formula XI-E can be prepared for example by a Wittig type reaction of a carbonyl compound of general formula XXIII a compound of the general formula XXXV wherein G² is halide, especially —Br or —I. This reaction is well described in the literature (e.g. Maryanoff, B. E. et al. Chem. Rev. 89 (1989) 863-927) and involves formation of a phosphonium salt with triphenylphosphine and the halide XXXV, its deprotonation with a suitable base e.g. sodium hydride or n-butyllithium to form an ylide and its reaction with the carbonyl compounds of formula XXIII to provide alkenes of formula XI-E under elimination of triphenylphosphine oxide.

Another method for the preparation of compounds of formula XI-E is a Horner-Wadsworth-Emmons type reaction of carbonyl compounds of formula XXIII with halides of formula XXXV, which is also very well described in the literature (e.g. Wadsworth, W. S., et al., J. Am. Chem. Soc. 83

(1961) 1733). It involves formation of an alkylphosphonic ester with trialkyl phosphite and a halide of formula XXXV in a Michael-Arbuzov type reaction, its deprotonation with a suitable base e.g. sodium hydride or n-butyllithium to form a phosphonate carbanion and its reaction with the carbonyl compounds of formula XXIII to provide alkenes of formula XI-E under elimination of a phosphate anion.

(E-2) The halides of formula XXXVI ($G^3$ is —Br, —I) can be prepared from the alcohol XXX by reactions well known to someone skilled in the art, e.g. by treatment with $CBr_4$ and $PPh_3$ in a suitable solvent e.g. dichloromethane or acetonitrile.

(E-3) These halides XXXVI ($G^3$ is —Br, —I) can be converted in a Wittig or Horner-Wadsworth-Emmons type reaction as described in section (E-1) with a carbonyl compound of formula XXXVII to compounds of formula XI-E.

(E-4) Another method for the preparation of XI-E is a cross coupling reaction for example of Suzuki type or Stille type between compound XXXVIII ($G^4$ is halogen, especially Br, Cl or I) and a compound of the general formula XXXIX wherein L is a boronic acid, boronic acid pinacolester and the like or L is trialkylstannane (e.g. $Me_3Sn$ or $Bu_3Sn$). See e.g. Wright, S. W., et al., J. Org. Chem. 59 (1994) 6095-6097; Mueller, H., and Tschierske, C., J. Chem. Soc., Chem. Commun. 6 (1995) 645-646, or Hanessian, S., et al., J. Org. Chem. 68 (2003) 7204-7218.

(E-5) Another method for the preparation of XI-E is a palladium catalyzed coupling reaction for example of Heck type between compound of formula XL ($G^5$ is e.g. Br, I or OTf) and a compound of the general formula IXL (See e.g. Heck, R. F., et al., J. Org. Chem. 37 (1972) 2320-2322).

An object of the present invention are pharmaceutical compositions containing a pharmacologically effective amount of one or more compounds of formula I in a mixture with pharmaceutically acceptable excipients and/or diluents.

According to a further aspect of the invention there is provided a medicament containing one or more compounds of the formula I as active ingredients together with pharmaceutically acceptable adjuvants. Such medicaments or pharmaceutical compositions may be in a form suitable for oral administration, for example as tablets, coated tablets, dragées, capsules, solutions emulsions or suspensions; for parenteral injections (including intravenous, subcutaneous, intramuscular, intravascular or infusion) as a sterile solution, suspension or emulsion; for topical administration as an ointment or cream or for rectal administration as a suppository. These pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions can comprise the following:

| Item | Ingredients | Mg/Tablet | |
|---|---|---|---|
| 1 | Compound of formula (I) | 25 | 100 |
| 2 | Anhydrous Lactose | 73 | 35 |
| 3 | Croscarmellose Sodium | 6 | 8 |
| 4 | Povidone K30 | 5 | 6 |
| 5 | Magnesium Stearate | 1 | 1 |
| | Total Weight | 140 | 150 |

Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Another pharmaceutical preparation is e.g. a micro-suspension of the compounds according to formula I. To obtain said micro-suspension the following materials were used:

An aqueous solution of 7.5% modified gelatine XF 20 (Braun) per injection (dissolved, filtered with a pore size of 0.45 µm and autoclaved), filters (custom made, mesh size 100 µm), filter holder, coupling, washed glass beads with a diameter of 0.25 mm and heat sterilised Retsch mills.

For the preparation of a typical batch 6244 mg of a compound of formula (I) were weighted into two 50 ml bottle flasks with 30 g glass beads, dispersed with a spatulum and vortexed. Then 10 ml gelatine vehicle were added to each bottle. The bottles were vortexed, capped and wrapped in aluminium foil for light protection. The contents was milled for 14 hours at 30/s in a Retsch mill. The micro-suspension was then extracted from the beads with two layers of filter (100 µm) on a filter holder, coupled to a recipient vial by centrifugation at 400 g during two minutes and including six washing steps, to give a final volume of 130 ml.

After homogenisation, the content was determined by HPLC to be 45.7 mg/ml which corresponds to a yield of 95%. The micro-suspension was diluted with 18.6 ml to give a final concentration of 40 mg/ml. The obtained spherical, granule-like particles show diameters between 1 and 5 µm as determined by microscopy. For storage, the micro-suspension was filled into sterile vials, capped, labelled and kept at −20° C. Before use, the micro-suspension must be homogenised vigorously by vortex.

The thiophene dicarboxylic acid derivative will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-100 mg/kg is employed. However the daily dose will necessarily be varied depending upon the host treated, the particular route of administration, and the severity of the illness being treated. Accordingly the optimum dosage may be determined by the practitioner who is treating any particular patient.

Pharmacological Activity

To show the activity of the compounds according to this invention, their effects on a human colon carcinoma cell line was evaluated using a standard MTT-assay. MTT (3-(4,5-dimethylthiazol-2-yl)-2,5-diphenyl tetrazolium bromide) is widely used for the quantitative determination of cytotoxic effects or in vitro chemosensitivity of tumor cells. The assay is based on the cleavage of the yellow tetrazolium salt (MTT) to purple formazan crystals by metabolic active cells. For details, see Rubinstein, L. V., et al., J. Natl. Cancer Inst. 82 (1990) 1113-1118.

We proceeded as follows: HT-29 cells (human colon carcinoma cell line, ATCC-No. HTB-38) were cultivated in RPMI 1640 medium with GlutaMAX™ I (Invitrogen, Cat-No. 61870-010), 2.5% fetal calf serum (FCS, Sigma Cat-No. F4135 (FBS)), 2 mM glutamine, 100 units/ml penicillin, 100 µg/ml streptomycin (=Pen/Strep from Invitrogen Cat. No. 15140). For the assay the cells were seeded in 384 well plates, 900 cells per well, in the same medium. At the next day, the compounds (dissolved 10 mM in DMSO) were added in various concentrations ranging from 30 µM to 1.5 nM. After 5 days, the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37° C., 5% CO2. During this incubation time purple formazan crystals are formed. After addition of the solubilization solution (20% Sodium Dodecyl Sulfate (SDS) in 0.02 M HCl) the plates were incubated overnight at 37° C., 5% CO2. After careful mixing, the plates were measured in Victor 2 (scanning multiweil spectrophotometer, Wallac) at 550 nm.

A decrease in number of living cells results in a decrease in the total metabolic activity in the sample. The decrease directly correlates to the amount of purple colour resulting from the solubilization of the purple formazan crystals. Determination of IC90 was done using XL-fit (XLfit software (ID Business Solution Ltd., Guilford, Surrey, UK)).

The reference compound has the following structure:

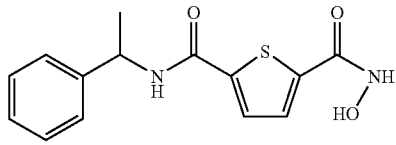

| Compounds according to this invention | IC90 HT29 [µM] |
|---|---|
| Reference compound | 1.12 |
| Example 1-1 | 0.69 |

An embodiment of the present invention is a medicament, as defined hereinbefore, for the inhibition of tumor cell proliferation by induction of histone acetylation in said tumor cell.

Another embodiment of the present invention is a medicament, as defined hereinbefore, for the treatment of neoplasms of the hematopoetic and lymphatic system.

Still another embodiment of the present invention is a medicament, as defined hereinbefore, for the treatment of cancer.

Still another embodiment of the present invention is a medicament as defined herein before for the treatment of colon-, breast-, lung-, prostate-, rectal-, stomach-, bladder-, pancreatic- or ovarian cancer.

Yet another embodiment of the present invention is the use of one or more compounds of formula I for the manufacture of medicaments for the inhibition of tumor cell proliferation by induction of histone acetylation in said tumor cell.

Yet another embodiment of the present invention is the use of one or more compounds of formula I for the manufacture of medicaments for treatment of cancer.

Yet another embodiment of the present invention is the use of one or more compounds of formula I for the manufacture of medicaments for treatment of colon-, breast-, lung-, prostate-, rectal-, stomach-, bladder-, pancreatic- or ovarian cancer.

Yet another embodiment of the present invention is the use of one or more compounds of formula I for the manufacture of medicaments for treatment of neoplasms of the hematopoetic and lymphatic system.

Yet another embodiment of the present invention is a method for inhibiting tumor cell proliferation by induction of histone acetylation in a tumor cell, due to administering to said tumor cell an effective amount of one or more compounds of formula I. According to a further feature of this aspect of the invention there is provided a method for producing an anti-cell-proliferation effect in a warm-blooded animal, such as man, in need of such treatment which comprises administering to said animal an effective amount of an thiophene dicarboxylic acid derivative as defined hereinbefore.

Therefore, still another embodiment of the present invention is the method as described above, wherein the tumor is colon-, breast-, lung-, prostate-, rectal-, stomach-, bladder-, pancreatic- or ovarian cancer.

According to a more preferred aspect of the present invention there is provided an compound of the formula I as defined hereinbefore for use in a method of treatment of the human or animal body by therapy. We have now found that the said compounds of the present invention possess anti-cell-proliferation properties which are believed to arise from their histone deacetylase inhibitory activity. Accordingly the compounds of the present invention provide a method for treating the proliferation of malignant cells. Accordingly the compounds of the present invention are expected to be useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

The anti-cell-proliferation treatment defined hereinbefore may be applied as a sole therapy or may involve, in addition to the thiophene dicarboxylic acid derivative of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antiestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, Cancer: Principles & Practice of Oncology, Vincent T. DeVita, Jr., Samuel Hellmann, Steven A. Rosenberg; 5th ed., Lippincott-Raven Publishers, 1997. Such conjoint treatment may be achieved by way of the simultaneous, sequential or separate dosing of individual components of the treatment. According to this aspect of the invention there is provided a pharmaceutical product comprising a thiophene dicarboxylic acid derivative of the formula I as defined hereinbefore and an additional anti-tumor substance as defined hereinbefore for the conjoint treatment of cancer.

The following examples and references are provided to aid the understanding of the present invention, the true scope of which is set forth in the appended claims. It is understood that modifications can be made in the procedures set forth without departing from the spirit of the invention.

EXAMPLE 1

Step 1: 1-[4-(4-trifluoromethoxy-benzyloxy)-phenyl]-ethanone

To a mixture of 300.0 mg (2.203 mmol) 4-hydroxyacetophenone and 305 mg (2.207 mmol) potassium carbonate in 15 ml acetone was added 868.7 mg (3.304 mmol) 4-(trifluoromethoxy)benzylbromide dropwise and heated under reflux for 1 d. The solvent was evaporated and to the residue was added ethyl acetate. The organic phase was washed with 1M aqueous HCl solution and water, dried over magnesium sulfate. The solvent was evaporated and the residue was subjected to silica gel chromatography (ethyl acetate/n-heptane 1:2) to yield 552 mg (1.779 mmol) 1-[4-(4-trifluoromethoxy-benzyloxy)-phenyl]-ethanone.

Step 2: 1-[4-(4-Trifluoromethoxy-benzyloxy)-phenyl]-ethylamine

To a mixture of 552.0 mg (1.779 mmol) 1-[4-(4-trifluoromethoxy-benzyloxy)-phenyl]-ethanone and molecular sieves in 10 ml methanol were added 1679.0 mg (21.35 mmol) ammonium acetate and 78.0 mg (1.241 mmol) sodium cyanoborohydride and the reaction mixture was stirred 26 h (HPLC control) at 50° C. After cooling to room temperature, the molecular sieves were filtered off and washed with methanol. The solvent of the combined filtrates was evaporated and diethyl ether and water were added to the residue. While stirring the mixture was acidified with 6N aqueous HCl solution to pH2. The aqueous phase was separated and the organic phase was extracted two times with 1N aqueous HCl solution. Ethyl acetate was added to the combined aqueous phases and the mixture was basified with 6N NaOH to pH 10. The organic phase was separated and the aqueous phase was extracted two more times with ethyl acetate. The combined organic phases were dried over MgSO4 and the solvent evaporated at reduced pressure to afford 268.0 mg (0.861 mmol) 1-[4-(4-trifluoromethoxy-benzyloxy)-phenyl]-ethylamine.

Step 3: 5-{1-[4-(4-Trifluoromethoxy-benzyloxy)-phenyl]-ethylcarbamoyl}-thiophene-2-carboxylic acid methyl ester To a solution of 160.0 mg (0.859 mmol) thiophene-2,5-dicarboxylic acid monomethyl ester in 25 ml dichloromethane were added 253.0 mg (1.293 mmol) N'-(3-dimethylaminopropyl)-N-ethylcarbodiimide hydrochloride, 175 mg (1.295 mmol) 1-hydroxybenzotriazole hydrate and 130.7 g (1.291 mmol) triethylamine. After 30 min at room temperature 268.0 mg (0.861 mmol) 1-[4-(4-trifluoromethoxy-benzyloxy)-phenyl]-ethylamine were added. The reaction mixture was stirred for 6.5 h. The solvent was evaporated, to the residue was added ethyl acetate and the organic phase was extracted with saturated aqueous NaHCO$_3$ solution and with water. The organic phase was dried over MgSO$_4$ and the solvent was evaporated. The residue was triturated with diisopropyl to provide 249 mg (0.519 mmol) 5-{1-[4-(4-trifluoromethoxy-benzyloxy)-phenyl]-ethylcarbamoyl}-thiophene-2-carboxylic acid methyl ester.

Step 4: Thiophene-2,5-dicarboxylic acid 2-hydroxyamide 5-({1-[4-(4-trifluoromethoxy-benzyloxy)-phenyl]-ethyl}-amide) (Compound 1-1)

To a solution of 249 mg (0.519 mmol) 5-{1-[4-(4-Trifluoromethoxy-benzyloxy)-phenyl]-ethylcarbamoyl}-thiophene-2-carboxylic acid methyl ester and 2.597 ml (5.194 mmol) of a 2M solution of hydroxylamine in methanol were added 34.5 mg (0.523 mmol) potassium hydroxide in little methanol. After 4 h at room temperature (rt) the reaction mixture was filtered and the solid was washed with methanol. The filtrate was treated with dry ice to lower the pH value to almost neutral. Stirring was continued for 15 min and the formed precipitate was filtered off. The solid was washed with methanol and the solvent of the combined organic filtrates was evaporated. The residue was triturated with diisopropylether and water to yield 126 mg (0.244 mmol) Thiophene-2,5-dicarboxylic acid 2-hydroxyamide 5-({1-[4-(4-trifluoromethoxy-benzyloxy)-phenyl]-ethyl}-amide) (Compound 1-1): calculated MW 480.74, found MW (M+H) 481.0; $^1$H-NMR (400 MHz, d6-DMSO): δ=8.87 (d, 1H), 7.81 (m, 1H), 7.56 (m, 3H), 7.38 (m, 2H), 7.30 (m, 2H), 6.97 (m, 2H), 5.12 (s, 2H), 5.07 (t, 1H), 1.45 (d, 3H)

EXAMPLE 2

Step 1: 1-(4-Nitro-phenyl)-ethylamine

The title compound was prepared in an analogous manner to that described in example 1, step 2 from 4-nitroacetophenone (reaction time 3d).

Step 2: 5-[1-(4-Nitro-phenyl)-ethylcarbamoyl]-thiophene-2-carboxylic acid methyl ester The title compound was prepared in an analogous manner to that described in example 1, step 3 from 1-(4-nitro-phenyl)-ethylamine and thiophene-2,5-dicarboxylic acid monomethyl ester.

Step 3: 5-[1-(4-Amino-phenyl)-ethylcarbamoyl]-thiophene-2-carboxylic acid methyl ester A mixture of 500 mg (1.497 mmol) 5-[1-(4-Nitro-phenyl)-ethylcarbamoyl]-thiophene-2-carboxylic acid methyl ester, 200 mg palladium on charcoal (10%), 10 ml methanol and 5 ml THF was hydrogenated at 30 mbar for 3 h. The catalyst was filtered off, the solvent was evaporated to give 5-[1-(4-amino-phenyl)-ethylcarbamoyl]-thiophene-2-carboxylic acid methyl ester.

Step 4: 5-{1-[4-(3-Methyl-benzylamino)-phenyl]-ethylcarbamoyl}-thiophene-2-carboxylic acid methyl ester A mixture of 304.0 mg (1.0 mmol) 5-[1-(4-amino-phenyl)-ethylcarbamoyl]-thiophene-2-carboxylic acid methyl ester, 120.0 mg (1.0 mmol) m-tolualdehyde and 2 ml ethanol was heated under reflux for 1 h. The solvent was evaporated and 3 ml THF and 315 mg (5.0 mmol) sodium cyanoborohydride were added to the residue. After 18 h 5 ml aqueous ammonium chloride solution and 10 ml water were added. The aqueous phase was extracted with dichloromethane, the combined organic phases were dried over magnesium sulfate, the solvent was evaporated and the residue subjected to silica gel chromatography (ethyl acetate/petrol ether 1:1) to yield 175 mg (0.43 mmol) 5-{1-[4-(3-Methyl-benzylamino)-phenyl]-ethylcarbamoyl}-thiophene-2-carboxylic acid methyl ester.

Step 5: Thiophene-2,5-dicarboxylic acid 2-hydroxyamide 5-({1-[4-(3-methyl-benzylamino)-phenyl]-ethyl}-amide) (Compound 2-1)

The title compound was prepared in an analogous manner to that described in example 1, step 4 from 5-{1-[4-(3-methyl-benzylamino)-phenyl]-ethylcarbamoyl}-thiophene-2-carboxylic acid methyl ester. Compound 2-1: calculated MW 409.51, found MW (M+H) 410.0; $^1$H-NMR (400 MHz, d6-DMSO): δ=8.56 (d, 1H), 7.69 (m, 1H), 7.31 (m, 1H), 7.16 (m, 3H), 7.03 (m, 3H), 6.51 (m, 2H), 6.13 (m, 1H), 4.96 (t, 1H), 4.19 (d, 2H), 2.27 (s, 3H), 1.39 (d, 3H)

LIST OF REFERENCES

Aranyos, A., et al., J. Am. Chem. Soc. 121 (1999) 4369-4378
Bastin, R. J., et al., Organic Proc. Res. Dev. 4 (2000) 427-435
Brown, H. C., et al., J. Am. Chem. Soc. 110 (1988) 1539-1546
Chan, D. M. T., et al., Tetrahedron Lett. 39 (1998) 2933-2936
Chen, C.-P., et al., Tetrahedron Lett. 32 (1991) 7175-7178
Corey, E. J., et al., Angew. Chemie 110 (1998) 2092-2118
DeVita, V. T., Hellmann, S. and Rosenberg, S. A.; Cancer: Principles & Practice of Oncology, 5th ed., Lippincott-Raven Publishers (1997)
Evans, D. A., et al., Tetrahedron Lett. 39 (1998) 2937-2940
Goddard, J., et al., Heterocycl. Chem. 28 (1991) 17
Hanessian, S., et al., J. Org. Chem. 68 (2003) 7204-7218
Heck, R. F., et al., J. Org. Chem. 37 (1972) 2320-2322
Houben-Weyl, "Methoden der organischen Chemie", Vols. XV/1 and XV/2, Georg Thieme Verlag, Stuttgart
Iglesias, L. E., et al., Tetr. Asym. 8 (1997) 2675-2677
Kinbara, K., et al., J. Chem. Soc., Perkin Trans. 2 (2000) 1339-1348
Kwong, F. Y., Org. Lett. 4 (2002) 581-584
Lam, P. Y. S. et al., Tetrahedron Lett. 39 (1998) 2941-2944
Louie, J., et al., J. Org. Chem. 62 (1997) 1268-1273
Mann, G., et al., J. Am. Chem. Soc. 120 (1998) 827-828
Marcoux, J.-F., et al., J. Am. Chem. Soc. 119 (1997) 10539-10540
Marks, P. A., et al., J. Nat. Cancer Inst. 92 (2000) 1210-1216
Maryanoff, B. E., et al., Chem. Rev. 89 (1989) 863-927
Mitsunobu, O., Synthesis 1 (1981) 1-28
Mueller, H., and Tschierske, C., J. Chem. Soc., Chem. Commun. 6 (1995) 645-646
Noyori, R., et al., Angew. Chem. 113 (2001) 40-75
Pallavicini, M., Tetr. Asym. 12 (2001) 2489-2495
Palucki, M., et al., J. Am. Chem. Soc. 119 (1997) 3395-3396
Rasor, P., and Voss, E., Applied Catalysis A: General 221 (2001) 145-158
Smith, H. E., et al., J. Am. Chem. Soc. 105 (1983) 1578-1584
Stahl, P. H., and Wermuth, G., (editors), Handbook of Pharmaceutical Salts, Verlag Helvetica Chimica Acta (VHCA), Zürich, (2002)
Synth. Commun. 1998, 28(21), 4067
U.S. Pat. No. 2,680,731
U.S. Pat. No. 4,983,771
U.S. Pat. No. 5,369,108
Wadsworth, W. S., et al., J. Am. Chem. Soc. 83 (1961) 1733
Wiegers, A., and Scharf, H.-D., Tetr. Asym. 7 (1996) 2303-2312
WO 01/38322
WO 01/70675
WO 02/22577
WO 03/011851
WO 03/066579
WO 03/075929
WO 03/076395
WO 03/076400
WO 03/076401
WO 03/076421
WO 03/076422
WO 03/076430
WO 03/076438
WO 03/087066
WO 2004/013130
WO 98/55449
Wolfe, J. P., et al., J. Am. Chem. Soc. 119 (1997) 6054-6058
Wright, S. W., et al., J. Org. Chem. 59 (1994) 6095-6097
Yamazaki, N., et al., Tetrahedron Lett. 42 (2001) 5029-5032
Yeager, G. W., et al., Synthesis 1 (1995) 28-30
Yin, J. et al., Org. Lett. 4 (2002) 3481-3484

The invention claimed is:

1. The compounds according to formula I and all pharmaceutically acceptable salts thereof wherein formula I is:

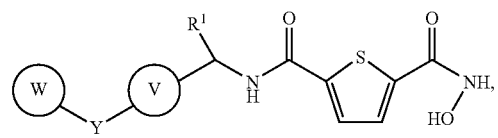

formula I wherein:
(a) $R^1$ is alkyl, which is optionally substituted one or more times by halogen;
(b) V is phenylene or heteroarylene;
(c) Y is selected from the group consisting of:
  (1) —O—;
  (2) —O—CHR$^2$—;
  (3) -alkylene-O—;
  (4) -alkylene-O—CHR$^2$—;
  (5) —NH—;
  (6) —NH—CHR$^2$—;
  (7) -alkylene-NH—;
  (8) -alkylene-NH—CHR2—; and
  (9) -alkenylene-;
(d) $R^2$ is alkyl or hydrogen; and (e) W is selected from the group consisting of:
  (1) a saturated carbocyclic group;
  (2) a saturated heterocyclic group;
  (3) a heteroaryl group; and
  (4) a phenyl group, which is substituted one to three times by alkyl, halogen, —O-alkyl, —S(O)$_2$-alkyl, —NH(alkyl) or —N(alkyl)$_2$; wherein the alkyl group is optionally substituted with one or more halogen atoms.

2. The compounds according to claim 1, wherein:
  (a) Y is -alkylene-O— or-alkylene-NH—; and
  (b) W is a phenyl group, which is substituted one to three times by alkyl, halogen, —O-alkyl, —S(O)$_2$-alkyl, —NH(alkyl) or —N(alkyl)$_2$; wherein the alkyl group is optionally substituted with one or more halogen atoms.

3. The compounds according to claim 1, wherein:
  (a) V is phenylene;
  (b) Y is -alkylene-O— or -alkylene-NH—; and
  (c) W is a phenyl group, which is substituted one to three times by alkyl or —O -alkyl; wherein the alkyl group is optionally substituted with one or more halogen atoms.

4. The compounds according to claim 3 wherein R$^1$ is methyl.

5. The compounds according to claim 3, wherein Y is -alkylene-O—.

6. The compounds according to claim 3, wherein Y is -alkylene-NH—.

7. The compounds according to claim 3, wherein W is a phenyl group substituted once by —OCF$_3$.

8. The compounds according to claim 3, wherein W is a phenyl group substituted once by —CH$_3$.

9. A compound according to claim 1 wherein the compound is Thiophene-2,5-dicarboxylic acid 2-hydroxyamide 5-({1-[4-(4-trifluoromethoxy-benzyloxy)-phenyl]-ethyl}-amide).

10. A compound according to claim 1 wherein the compound is Thiophene-2,5-dicarboxylic acid 2-hydroxyamide 5-({1-[4-(3-methyl-benzylamino)-phenyl[-ethyl}-amide).

11. A process for the manufacture of the (R)- or (S)-enantiomers or racemates of the compounds of formula I of claim 1 by:

(a) reacting compounds of formula IV:

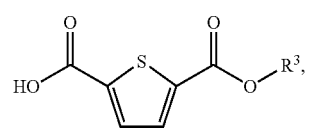

formula IV wherein R$^3$ is an alkyl group;
with racemic amines, or (R)-amines or (S)-amines of formula X:

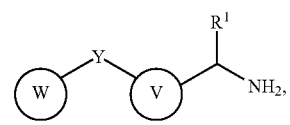

formula X wherein V, W, Y and R$^1$ are defined according to claim 1, in the presence of a suitable activating agent, to obtain the compounds of formula XI:

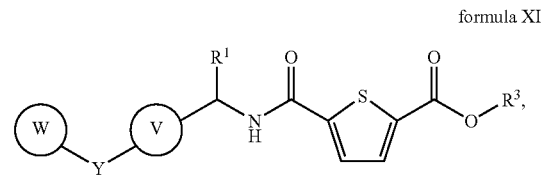

formula XI wherein V, W, Y and R$^1$ are defined according to claim 1 and R$^3$ is an alkyl group;

(b) treating said compounds of formula XI with hydroxylamine to obtain the compounds of formula I as defined in claim 1; and (c) optionally transforming said compounds into their pharmaceutically acceptable salts.

12. A pharmaceutical composition comprising a compound of claim 1 and one or more pharmaceutically acceptable excipients, diluents, or adjuvants.

* * * * *